US009707251B2

(12) United States Patent
Mukhopadhyay et al.

(10) Patent No.: US 9,707,251 B2
(45) Date of Patent: *Jul. 18, 2017

(54) SILOXANE-BASED ARTIFICIAL BLOCKAGE TO CONTROL BLEEDING

(75) Inventors: Kausik Mukhopadhyay, College Park, MD (US); Krishnaswamy Kasthuri Rangan, Fairfax, VA (US); Tirumalai Srinivas Sudarshan, Vienna, VA (US)

(73) Assignee: MATERIALS MODIFICATION, INC., Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/584,852

(22) Filed: Aug. 14, 2012

(65) Prior Publication Data
US 2012/0308509 A1  Dec. 6, 2012

Related U.S. Application Data

(63) Continuation-in-part of application No. 12/314,718, filed on Dec. 16, 2008, now Pat. No. 8,852,558, which is a continuation-in-part of application No. 12/073,822, filed on Mar. 11, 2008, now Pat. No. 8,828,358.

(60) Provisional application No. 61/523,401, filed on Aug. 14, 2011.

(51) Int. Cl.
| | |
|---|---|
| A61L 15/18 | (2006.01) |
| A61L 15/20 | (2006.01) |
| A61L 26/00 | (2006.01) |
| A61K 33/40 | (2006.01) |
| A61K 31/74 | (2006.01) |
| A61L 15/42 | (2006.01) |
| A61K 31/80 | (2006.01) |
| A61L 24/00 | (2006.01) |

(52) U.S. Cl.
CPC .............. *A61K 31/74* (2013.01); *A61K 31/80* (2013.01); *A61L 15/425* (2013.01); *A61L 24/001* (2013.01); *A61L 24/0015* (2013.01); *A61L 24/0089* (2013.01); *A61L 26/0009* (2013.01); *A61L 26/0085* (2013.01); *A61L 2300/11* (2013.01); *A61L 2300/404* (2013.01); *A61L 2400/04* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 2,598,127 A | 5/1952 | Keckler | |
| 4,030,504 A | 6/1977 | Doyle | |
| 4,331,653 A | 5/1982 | Brown et al. | |
| 4,377,159 A | 3/1983 | Hansen | |
| 4,948,575 A | 8/1990 | Cole et al. | |
| 4,987,893 A | 1/1991 | Salamone et al. | |
| 5,103,812 A | 4/1992 | Salamone et al. | |
| 5,153,231 A | 10/1992 | Bouquet et al. | |
| 5,336,163 A | 8/1994 | DeMane et al. | |
| 5,480,653 A * | 1/1996 | Aguadisch ........... A61K 9/2036 424/425 |
| 5,507,721 A | 4/1996 | Shippert | |
| 5,667,501 A | 9/1997 | Fowler et al. | |
| 5,846,567 A | 12/1998 | Kalloo et al. | |
| 6,054,122 A | 4/2000 | MacPhee et al. | |
| 6,534,016 B1 | 3/2003 | Cohen et al. | |
| 6,627,216 B2 | 9/2003 | Brandt et al. | |
| RE38,431 E | 2/2004 | Miekka et al. | |
| 6,958,154 B2 | 10/2005 | Andolino Brandt et al. | |
| 6,964,782 B1 | 11/2005 | Smith et al. | |
| 7,101,862 B2 | 9/2006 | Cochrum et al. | |
| 7,196,054 B1 | 3/2007 | Drohan et al. | |
| 7,226,615 B2 | 6/2007 | Yüksel et al. | |
| 7,347,850 B2 | 3/2008 | Sawhney | |
| 7,641,893 B2 | 1/2010 | Salamone et al. | |
| 7,795,326 B2 | 9/2010 | Salamone et al. | |
| 7,838,716 B2 | 11/2010 | De Luis et al. | |
| 8,025,650 B2 | 9/2011 | Anderson et al. | |
| 2003/0224054 A1 | 12/2003 | Gibbins et al. | |
| 2005/0070616 A1 | 3/2005 | Champ et al. | |
| 2006/0142684 A1 | 6/2006 | Shanbrom | |
| 2006/0233887 A1* | 10/2006 | Day ............................ 424/602 |
| 2007/0154564 A1* | 7/2007 | Stucky .................. A61K 33/00 424/603 |
| 2007/0203062 A1 | 8/2007 | Ellis-Behnke et al. | |

(Continued)

FOREIGN PATENT DOCUMENTS

WO    WO2007/088038 A1    8/2007

OTHER PUBLICATIONS

Office Action dated Oct. 24, 2013, in U.S. Appl. No. 12/314,718, filed Dec. 16, 2008.
Office Action dated Oct. 24, 2013, in U.S. Appl. No. 12/073,822, filed Mar. 11, 2008.
PCT International Search Report and the Written Opinion in International App. No. PCT/US2012/050716 dated Oct. 19, 2012 (13 pp.) with Search History (11 pp.).
B.S. Kheirabadi, D. Tuthill, R. Pearson, V. Bayer, D. Beall, W. Drohan, M. J. MacPhee, J.B. Holcomb, Metabolic and Hemodynamic Effects of $CO_2$ Pneumoperitoneum in a Controlled Environment, *Journal of Trauma Injury, Infection and Ciritcal Care*, 50, 1031-1043 (2001).

(Continued)

*Primary Examiner* — Kevin S Orwig
(74) *Attorney, Agent, or Firm* — Jyoti C. Iyer

(57) ABSTRACT

Two siloxane-based mixtures combine to form a soft or semi-solid matrix for forming an artificial blockage to control bleeding, particularly moderate to severe bleeding. The first component includes a homogeneous mixture or solution that includes a polymeric matrix, a surfactant, filler(s) and metal compound(s). The second component includes a homogeneous mixture or solution that includes a polymer(s), a filler(s), a surfactant, and hydrogen peroxide. The combination of the two components is carried out with adequate mixing using mechanical and micro-kinetic mixing mechanisms and can be performed in a field-ready delivery device.

29 Claims, 9 Drawing Sheets

(56) References Cited

U.S. PATENT DOCUMENTS

| | | | |
|---|---|---|---|
| 2009/0093550 | A1 | 4/2009 | Rolfes |
| 2009/0202617 | A1 | 8/2009 | Ward et al. |
| 2009/0210002 | A1 | 8/2009 | Salamone et al. |
| 2009/0232876 | A1 | 9/2009 | Montes et al. |
| 2009/0232877 | A1* | 9/2009 | Montes et al. ............... 424/447 |
| 2010/0063434 | A1 | 3/2010 | Naik |
| 2010/0100022 | A1 | 4/2010 | Greener et al. |
| 2010/0234784 | A1 | 9/2010 | Hartwell |
| 2010/0292626 | A1 | 11/2010 | Gundersen et al. |
| 2011/0046262 | A1 | 2/2011 | Bublewitz et al. |
| 2011/0092871 | A1 | 4/2011 | Fabo et al. |
| 2011/0178451 | A1 | 7/2011 | Robinson et al. |
| 2011/0237994 | A1 | 9/2011 | Russ et al. |
| 2011/0275972 | A1 | 11/2011 | Rosenberg |

OTHER PUBLICATIONS

J.B. Holcomb, J.M. McClain, A.E. Pusateri, D. Beall, J.M. Macaitis, R.A. Harris, M. J. MacPhee, J.R. Hess, Fibrin Sealant Foam Sprayed Directly on Liver Injuries Decreases Blood Loss in Resuscitated Rats *Journal of Trauma Injury, Infection and Ciritcal Care*, 49, 246-250, (2000).

D.D. Tuthill, V. Bayer, A.M. Gallagher,W.N. Drohan, M.J. MacPhee, Assessment of Topical Hemostats in a Renal Hemorrhage Model in Heparinized Rats, *Journal of Surgical Research*, 95, 126-132 (2001).

Holcomb et al. Implications of a New Dry Fibrin Sealant Technology for Trauma Surgery, *Surgical Clinics of North America*, 77, 944-952 (1997).

H.B. Alam, G. B. Uy, D. Miller, E. Koustova T. Hancock, R. Inocencio, D. Anderson, O. Llorente, P. Rhee, Comparative Analysis of Hemostatic Agents in a Swine Model of Lethal Groin Injury, *The Journal of Trauma, Injury, Infection, and Critical Care*, 54, 1077-1082 (2003).

R.G. Ellis-Behnke, Y-X. Liang, D.K.C. Tay, P.W.F. Kau, G.E. Schneider, S. Zhang, W. Wu, K.-F. So, Nano Hemostat Solution: Immediate Hemostasis at the Nanoscale, *Nanomedicine: Nanotechnology, Biology, and Medicine*; 2 , 207-215 (2006).

M.W. Chan, S.D. Schwaitzberg, M. Demcheva, J. Vournakis, S. Finkielsztein, R.J. Connolly, Comparison of Poly-N-acetyl Glucosamine with Absorbable Collagen, and Fibrin Sealant for Achieving Hemostasis in a Swine Model of Splenic Hemorrhage, *Journal of Trauma Injury, Infection and Critical Care*, 48, 454-7 (2000).

I. Wedmore, J.G. McManus, A.E. Pusateri, J.B. Holcomb, Special Report on the Chitosan-based Hemostatic Dressing: Experience in Current Combat Operations, *The Journal of Trauma Injury, Infection and Critical Care*, 60, 655-658 (2006).

A. M. Pope, Editor, Fluid Resuscitation: State of the Science for Treating Combat Casualties and Civilian Injuries, The National Academy Press, (2000).

A.E. Pusateri,J.B. Holcomb, B.S. Kheirabadi,H.B. Alam, C.E. Wade, K.L. Ryan, Making Sense of the Preclinical Literature on Advanced Hemostatic Products, *The Journal of Trauma Injury, Infection and Critical Care*, 60, 674-682, (2006).

H.B. Alam, Z. Chen, A. Jaskille,R.I.L.C. Querol, E. Koustova, R. Inocencio, R. Conran, A. Seufert, N. Ariaban, K. Toruno, P. Rhee, Application of a Zeolite Hemostatic Agent Acheives 100% Survival in a Lethal Model of Complex Groin Injury in Swine, *The Journal of Trauma Injury, Infection and Critiacal Care*, 56, 974-983, (2004).

B.S. Kheirabadi, E.M. Acheson, R. Deguzman, J.L. Sondeen, K.L. Ryan, A. Delgado A, E.J. Dick Jr, J.B. Holcomb, Hemostatic Efficacy of Two Advanced Dressings in an Aortic Hemorrhage Model in Swine, *The Journal of Trauma Injury, Infection and Critical Care*, 59, 25-34 (2005).

J.G McManus, I. Wedmore, Modern Hemostatic Agents for Hemorrhage Control—A review and Discussion of Use in Current Combat Operations, *Business Briefing: Emergency Medicine Review*,76-79 (2005).

Li X, Xu A, Xie H, Yu W, Xie W, Ma X. Preparation of low molecular weight alginate by hydrogen peroxide depolymerization for tissue engineering. Carbohydrate Polymers 79 (2010) 660-664.

Palm, M.D. et al. Topical Hemostatic Agents: A Review. Dermatol. Surg. E-pub Jan. 31, 2008;34; 431-445.

Costa, S.A. et al. Enzyme Immobilization in Biodegradable Polymers for Biomedical Applications. Ch. 17 in Biodegradable Systems in Tissue Engineering and Regenerative Medicine; Rui Reis, ed. CRC Press; 2004; 301-323.

PCT International Search Report and the Written Opinion dated Feb. 26, 2010, in International App. No. PCT/US09/06536 (8 pp.).

Office Action (Restriction Requirement) dated Jul. 21, 2010, in U.S. Appl. No. 12/073,822, filed Mar. 11, 2008.

Office Action dated Jan. 12, 2011, in U.S. Appl. No. 12/073,822, filed Mar. 11, 2008.

Office Action (Final Rejection) dated Aug. 9, 2011, in U.S. Appl. No. 12/073,822, filed Mar. 11, 2008.

Office Action (Restriction Requirement) dated Sep. 29, 2010, in U.S. Appl. No. 12/314,718, filed Dec. 16, 2008.

Office Action dated Feb. 4, 2011, in U.S. Appl. No. 12/314,718, filed Dec. 16, 2008.

Office Action (Final Rejection) dated Aug. 10, 2011, in U.S. Appl. No. 12/314,718, filed Dec. 16, 2008.

Notice of Allowance dated Jun. 4, 2014, in U.S. Appl. No. 12/314,718, filed Dec. 16, 2008.

Notice of Allowance dated Jun. 6, 2014, in U.S. Appl. No. 12/073,822, filed Mar. 11, 2008.

Haller, G. et al. *Oxygen embolism after hydrogen peroxide irrigation of a vulvar abscess*, British Journal of Anaesthesia 88 (4): 597-9 (2002).

Shetty, K. *Hydrogen Peroxide Burn of the Oral Mucosa, The Annals of Pharmacotherapy*, vol. 40, p. 351, Feb. 2006.

Rackoff, W.R. et al. *Gas Embolism After Ingestion of Hydrogen Peroxide, Pediatrics*, vol. 85, No. 4, Apr. 1990, 593-594.

Li, Y. *Biological Properties of Peroxide-containing Tooth Whiteners, Food and Chemical Toxicology* 34 (1996) 887-904.

Giberson, T.P. et al. *Near-Fatal Hydrogen Peroxide Ingestion, Annals of Emergency Medicine*, 18:7, Jul. 1989, 778-779.

\* cited by examiner

SILOXANE-BASED ARTIFICIAL BLOCKAGE TO CONTROL BLEEDING

CROSS-REFERENCE TO RELATED APPLICATIONS

This is a continuation-in-part (CIP) application of U.S. application Ser. No. 12/314,718, filed Dec. 16, 2008, which is a continuation-in-part (CIP) application of U.S. application Ser. No. 12/073,822, filed Mar. 11, 2008, both of which are hereby incorporated herein in their entirety by reference. This application further claims the priority benefit of U.S. Provisional Patent Application Ser. No. 61/523,401, filed Aug. 14, 2011, which is also hereby incorporated herein in its entirety by reference.

FIELD AND BACKGROUND OF THE INVENTION

The present invention is generally directed to hemostatic compositions and methods employing the same, the delivery of agents into or unto wounds and/or body cavities, and more particularly to a composition and method for controlling bleeding at wound sites through the formation of an in situ obstruction to blood flow.

One frequent cause of death is the uncontrolled and unrestricted loss of blood due to traumatic injury, accidental or otherwise. Non-limiting examples of such wounds include punctures, lacerations, gashes, and tears in or on body parts. The blood loss can be internal or external to the body and, when not restricted or controlled immediately following the injury, can result in death. It is critical to restrict, arrest, or control the blood loss by creating a physical blockage over, against, or around the wound. Such blockages provide advantageous devices for use in stopping or controlling bleeding when administered by first responders such as paramedics, firefighters, lifeguards, and police officers, as well as in remote areas, on the battlefield, and after natural disasters, or in hospitals after intensive surgeries.

One body of work known to the inventors is that showing as assignee Rochal Industries LLP, which includes U.S. patent application Ser. No. 12/414,708 (US PG-Pub 2009/0210002) and U.S. Pat. Nos. 4,987,893; 5,103,812; 7,641,893; and 7,795,326. All involve siloxane or siloxane derivative based liquid or aerosol type bandages, but they lack the components of the invention disclosed herein and most notably, are not formed from a first and second mixture, as will become apparent from the disclosure of this invention, provided below.

ASPECTS OF THE INVENTION

The present disclosure is directed to various aspects of the present invention.

One aspect of the present invention is to provide a composition and method for reducing, restricting, and/or arresting, (collectively "controlling") hemorrhage from wounds, internal or external, in humans and other animals.

Another aspect of the present invention is to provide a composition and method for in situ formation of an artificial blockage to control bleeding.

Another aspect of the present invention is to provide a composition and method for in situ formation of a semi-solid matrix to control bleeding.

Another aspect of the present invention is to provide a composition and method for in situ formation of an artificial blockage to control moderate to severe bleeding.

Another aspect of the present invention is to provide a composition and method for in situ formation of a semi-solid matrix to control moderate to severe bleeding.

Another aspect of the present invention is to provide a composition and method for in situ formation of an artificial blockage or semi-solid matrix to control bleeding as to prelude to initiating the body's natural clotting cascade.

Another aspect of the present invention is to provide a composition and method for in situ formation of an artificial blockage or semi-solid matrix to control moderate to severe bleeding as to prelude to initiating the body's natural clotting cascade.

Another aspect of the present invention is to provide a composition and method which are especially suited for emergency situations where it is critical to control uncontrolled or unrestricted blood loss to prevent death. An artificial blockage or semi-solid matrix rendered at the blood loss site functions as an immediate hemostatic plug that controls the blood flow and allows the body's natural clotting cascade to take effect.

Another aspect of the present invention is to provide a composition made from two components or mixtures capable of forming a semi-solid blockage, particularly for reducing, restricting, and/or arresting (collectively "controlling") bleeding from internal or external wounds in humans and other animals.

Another aspect of the present invention is to provide a method of making a blockage agent substantially by adequately mixing two mixtures.

Another aspect of the present invention is to provide a field delivery-capable or portable device, which facilitates adequate mixing of two mixtures to form a combination composition capable of forming a blockage, especially in wounds, without following any complicated instructions or undertaking measurements to enable error-proof administration.

Another aspect of the present invention includes a two-component system for in situ formation of an artificial blockage to control moderate to severe bleeding, which includes:
  a) a first component including:
    i) about 10-100% by weight or volume of at least one siloxane polymer; ii) about 0-25% by weight or volume of at least one surfactant;
    iii) about 0-25% by weight or volume of at least one catalyst; and
    iv) about 0-30% by weight or volume of at least one metal compound;
  b) a second component including:
    i) about 10-100% by weight or volume of at least one siloxane polymer;
    ii) about 0-25% by weight or volume of at least one surfactant;
    iii) about 1-20% by weight or volume of hydrogen peroxide; and
    iv) about 0-10% by weight or volume of at least one particle filler.

Another aspect of the present invention includes a two-component system for in situ formation of an artificial blockage to control moderate to severe bleeding, which includes:
  a) a first component including:
    i) about 84% by weight or volume of at least one siloxane polymer;

ii) about 0.5-2% by weight or volume of at least one surfactant;
iii) about 0.5-3% by weight or volume of at least one catalyst; and
iv) about 12-18% by weight or volume of at least one metal compound;

b) a second component including:
i) about 82% by weight or volume of at least one siloxane polymer;
ii) about 0.5-2% by weight or volume of at least one surfactant;
iii) about 17.5% by weight or volume of hydrogen peroxide; and
iv) about 0.2% by weight or volume of at least one particle filler.

Another aspect of the present invention includes a hemostatic blockage composition formed in situ by using a two-component system to control moderate to severe bleeding. The system includes:

a) a first component including:
i) about 10-100% by weight or volume of at least one siloxane polymer;
ii) about 0-25% by weight or volume of at least one surfactant;
iii) about 0-25% by weight or volume of at least one catalyst; and
iv) about 0-30% by weight or volume of at least one metal compound;

b) a second component including:
i) about 10-100% by weight or volume of at least one siloxane polymer;
ii) about 0-25% by weight or volume of at least one surfactant;
iii) about 1-20% by weight or volume of hydrogen peroxide; and
iv) about 0-10% by weight or volume of at least one particle filler.

Another aspect of the present invention includes a hemostatic blockage composition formed in situ by using a two-component system to control moderate to severe bleeding. The system includes:

a) a first component including:
i) about 84% by weight or volume of at least one siloxane polymer;
ii) about 0.5-2% by weight or volume of at least one surfactant;
iii) about 0.5-3% by weight or volume of at least one catalyst; and
iv) about 12-18% by weight or volume of at least one metal compound;

b) a second component including:
i) about 82% by weight or volume of at least one siloxane polymer;
ii) about 0.5-2% by weight or volume of at least one surfactant;
iii) about 17.5% by weight or volume of hydrogen peroxide; and
iv) about 0.2% by weight or volume of at least one particle filler.

Another aspect of the present invention includes a method for in situ formation of an artificial blockage in a wound or body cavity to control moderate to severe bleeding, which includes:

a) providing a suitable amount of a first component including:
i) about 10-100% by weight or volume of at least one siloxane polymer;
ii) about 0-25% by weight or volume of at least one surfactant;
iii) about 0-25% by weight or volume of at least one catalyst; and
iv) about 0-30% by weight or volume of at least one metal compound;

b) providing a suitable amount of a second component, including:
i) about 10-100% by weight or volume of at least one siloxane polymer;
ii) about 0-25% by weight or volume of at least one surfactant;
iii) about 1-20% by weight or volume of hydrogen peroxide; and
iv) about 0-10% by weight or volume of at least one particle filler;

c) mixing the first and second components immediately prior to use in or adjacent the wound or body cavity; and d) allowing the mixture to penetrate the wound or body cavity and expand therein to form a matrix.

BRIEF DESCRIPTION OF THE DRAWINGS

One of the above and other aspects, novel features, and advantages will become apparent from the following detailed description of the preferred embodiment(s) of the invention, illustrated in the accompanying drawings, wherein.

DETAILED DESCRIPTION OF THE PREFERRED EMBODIMENT(S) OF THE INVENTION

Figure 1:
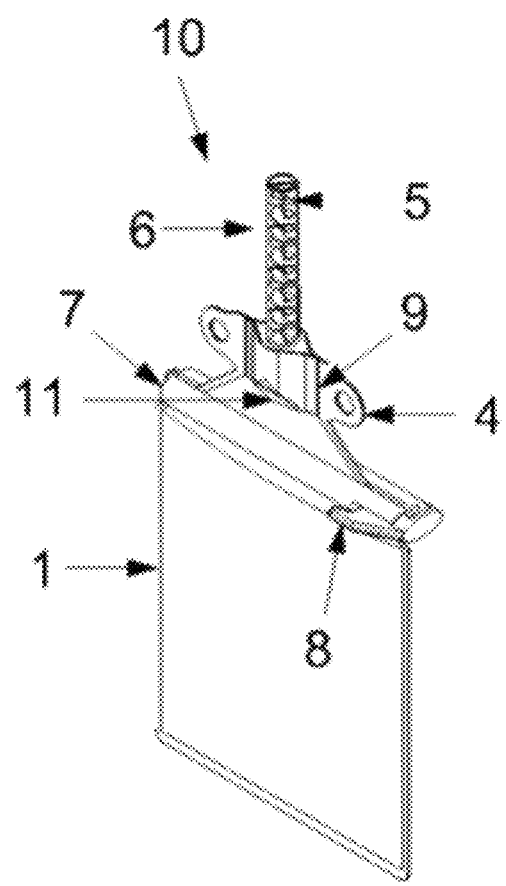
FIG. 1 is a perspective view of a delivery device according to a preferred embodiment of the present invention.

The composition of the present invention is referred to as a binary or two-part system which, upon adequate mixing and combination of the components in suitable quantities, forms a soft solid or semi-solid matrix capable of forming a blocking device, particularly useful in forming a hemostasis device.

The composition is formed from two solutions (or mixtures), which are kept separate until application and combination. Both solutions contain siloxane polymer(s). Preferably, one solution (designated for reference purposes only as "component B") contains a curing agent for the polymer(s), or a catalyst, such as platinum and compounds of platinum, tin and compounds of tin, or other metal compounds, capable of catalyzing or curing siloxane polymers optionally bound to a siloxane or a derivative. Salts of platinum and tin can also be used. Other noble metals, including palladium, rhodium and the like and their respective compounds, salts and complexes, can also be used as catalysts. The catalyst ranges from about 0-25%, or preferably about 0.5-3%, by weight or volume, of the component B.

Siloxane polymers are organosilicone compounds often referred to as silicones. Importantly, they are non-toxic and will not cause harm to biological systems, including humans and animals. Non-limiting examples include polydimethylsiloxane (PDMS), divinyltetramethyldisiloxane, methylhydrosiloxane, dimethylsiloxane, and combinations thereof. The ranges of siloxane polymer in component A include about 10-100%, preferably 75-85%, and more preferably about 82%, by weight or volume. In component B, the siloxane polymer ranges from about 10-100%, preferably about 75-90%, and more preferably about 84%, by weight or volume.

The first solution (component B) additionally contains a surfactant and a calculated combination of iron and iron compounds, and alkaline (Group II) elements and their compounds. Non-limiting examples of particle fillers in composition B include group II alkaline earth metal compounds include oxides, hydroxides, peroxides, suboxides, superoxides, mixed oxides, carbonates, hydrogen carbonates, phosphates, hydrogen phosphates, sulfates, hydrogen sulfates, nitrates, fluorides, chlorides, bromides, iodides, cyanates, isocyanates of magnesium, calcium, barium and strontium. The compounds mentioned herein, and used in component B can be a single compound or a mixture of compounds listed herein. Metal compounds in component B can range from 0%-30%, preferably 5%-25%, more preferably 12%-18%, by weight or volume.

One or more of the solutions additionally contains a granular additive or aggregate material. The second solution (designated for reference purposes only as "component A") additionally contains a surfactant and hydrogen peroxide.

The decomposition of hydrogen peroxide is an exothermic reaction. When the hydrogen peroxide-containing solution contacts with the alkaline salt/oxide and iron oxide containing mixture, the latter compounds serve as a catalyst for decomposing hydrogen peroxide into oxygen and water following the reaction: $H_2O_2 \rightarrow H_2O + O_2$. Importantly, hydrogen peroxide is completely or nearly completely reacted upon combination of the two mixtures, which reduces or avoids the possibility of the human or animal subject feeling pain as a result of hydrogen peroxide causing stinging in or on the wound site.

Figure 3:
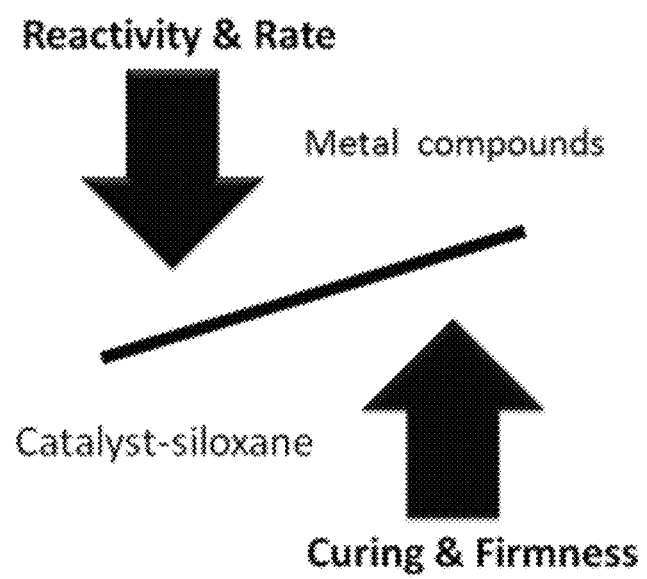
FIG. 3 is a schematic illustration of a process occurring during formation of a hemostatic polymeric or blocking agent according to a preferred embodiment of the present invention.

As described, iron compounds and Group II element salts or oxides both serve as catalysts in the decomposition of hydrogen peroxide. Importantly, however, iron oxide can be described as a negative co-catalyst or rate limiting step on the effect of the Group II oxides or salts. This rate limiting step controls the heat generated from the decomposition of hydrogen peroxide and avoids the composition applied in situ being too hot and burning or scalding the area it is applied to on a human or animal. This catalyst/co-catalyst effect is depicted in FIG. 3.

Moreover, Group II oxides or salts aid in releasing a curing agent bound to a siloxane upon disassociation. For instance, in an embodiment comprising platinum divinylpolymethylsiloxane, the platinum is the curing agent, which is aided by the Group II oxides or salts in unbinding.

The iron compounds can be any oxide of iron, including $Fe_2O_3$, $Fe_3O_4$, or FeO, or any salt of iron including but not limited to, iron chloride, iron nitrate, iron sulfate, and ammonium iron sulfate. $Fe_3O_4$ was found to work best and $Fe_2O_3$ was found to work well. However, $Fe_3O_4$ is in general more expensive to obtain and for this reason, $Fe_2O_3$ is the preferred oxide of iron used, as it accomplishes the task of the iron oxide in the most economical fashion.

The heat generated during the decomposition serves three purposes. First, it acts to speed up the polymerization and thus formation of the blocking device, and secondly acts to slow or restrict blood flow if the blocking device is applied about a wound. Finally, it decreases the viscosity of the first and second mixtures, facilitating easier combination.

The surfactant used in both mixtures acts to reduce agglomeration and resultant potential sedimentation of the components and consequently enhances the ability of the solutions to mix readily. The surfactant may be cationic, anionic, amphoteric or nonionic. Any chemical that helps in wetting, mixing of the various ingredients with the siloxane can be used. The non-limiting examples of such agents include, but not limited to, polyether, polyol-polyether mixture, fluoro surfactant or fluoro surfactant and polyether polymer, nonylphenoxypoly(ethylene oxy)ethanol, polyoxyethylene sorbitan monolaurate (Tween 20™), Igepal CO-530, Tergitol, Birj, polysiloxane-polyether copolymers or alkyl phenol ethoxylate. polyoxy ethylene sorbitan monopalmitate (Tween 40™), polyoxythylene sorbitan monostearate (Tween 60™), polyoxyethylene sorbitan monooleate (Tween 80™), and Triton X-100™. When the blocking agent is used as a hemostasis product, the use of a non-toxic surfactant is necessary. For this reason, Tween 20™ and Tween 80™ (Polysorbate 80) are preferable due to their established non-toxicity, acceptance in health, and low cost. The ranges of surfactant include about 0-25%, and preferably about 0.5-2%, by weight or volume.

The Group II metal oxides are contemplated as being replaced with any hydrogen peroxide decomposing compound. Such compounds include tin (Sn), Manganese (Mn), Nickel (Ni), Cobalt (Co), Titanium (Ti), and Chromium (Cr), as well as hydroxide (OH—) and sulfate.

The composition is made by combining the two mixtures. Adequate mixing of the two solutions is necessary to achieve the most desirable composition for the blocking agent. Most ideally, the composition formed is without significant foaming. Adequate mixing is ensured by microkinetic considerations, in addition to mechanical means.

When the two fluids (or mixtures) are combined, the curing agent of the first solution is unbound from its siloxane polymeric component, with the aid of oxides or salts of the metals. The curing agent acts upon the siloxane polymers found in both solutions and a soft solid matrix is formed. Without catalyst or curing agent, the curing into a soft solid matrix is completed in 72 to 96 hours—and unacceptably long time period to form a blocking agent, especially when used in an emergency situation to form a hemostasis product. With catalyst or curing agent used, a soft-solid matrix begins to form upon combination and is substantially set within 0 to 60 minutes.

The curing into a soft solid matrix is further enhanced by heat which reduces the curing time. It is noted that overly long and short curing times potentially make the final composition of the blocking agent too hard or too soft and especially not able to perform as a blocking agent to control blood loss.

As noted earlier, heat generated by the decomposition of hydrogen peroxide reduces the viscosity of the first and second mixtures, which facilitates easier mixing between them and ultimately best matrix composition. The first and second mixtures may be within 25% viscosity of one another from the outset so as to be best capable of mixing and combining.

Adequate mixing is made possible by both micro-kinetic and mechanical mixing means. The micro-kinetic mixing means are carried out by the inclusion of aggregate in on or both of the solutions. The aggregate is preferably a non-reactive compound of small size. Fumed silica ($SiO_2$) is a non-limiting but exemplary example of such an aggregate. Upon combination of the mixtures, the aggregate particles via their abrasive qualities act as local micro-stirrers which push, pull, carry, and intermingle the components of one of the solutions with the other.

At a macro scale, the mixing is carried out via the physical forcing of the solutions into a homogenous or semi-homogeneous mixture. Machine or human operator powered mixing methods include, by way of example, stirring, whisking, agitating, pushing, pulling, pumping, or shaking the combination of the first and second mixtures. The use of aggregate was found to improve mixing effectiveness by 15%-20%.

Trials were performed using mechanical mixing alone and micro-kinetic mixing in addition to mechanical mixing. The use of micro-kinetic mixing means enhanced the homogeneity of the mixture and advantageously decreased curing time.

Importantly, nearly all of the hydrogen peroxide was reacted following combination of the two mixtures or components. Less than 5% of the hydrogen peroxide was found to remain in the soft-solid matrix formed by the combination. A low amount of hydrogen peroxide in the final composition is further notable as it prevents stinging when the combination is made and the blocking agent is applied in or on the wound of a human or animal.

One method of preparing the first and second mixtures or components into a state ready to be combined is to stir them using common laboratory devices, such as a magnetic stirrer or overhead mixer for approximately 30 to 60 minutes. The mixtures are stirred separately. In the case of the second mixture containing hydrogen peroxide, the hydrogen peroxide is initially excluded from the other components and is added after approximately 30 to 50 minutes of stirring. Subsequently, the hydrogen-peroxide mixture is stirred for about an additional 20 to 35 minutes after addition of the hydrogen peroxide.

When the blocking agent is used as a hemostasis product to control bleeding, it is preferable that the composition be formed easily, without measurement, and in a relatively self-evident way that does not necessitate instruction or training; and that the mixing be performed adequately and quickly.

A method for accomplishing quick and adequate mixing involves combining and mixing the solutions in a device. Non-limiting examples of such devices, which would aid in mixing the combinations, include two-fluid aerosol delivery devices, two-fluid chambers, and two-fluid syringes for instance.

The instant invention combines the first and second mixtures in a device with mixing and delivery tip. The two solutions are pre-measured and held in two chambers isolated from one another by a wall. An operator squeezes the device to push the two solutions inside the two chambers simultaneously. The solutions are delivered substantially simultaneously into a tip from one or more openings at the end of the chambers, where mixing occurs. Preferably, a plurality of turbulators are disposed within the tip such that the solutions are sloshed, agitated, and/or moved about the turbulators within the confines of the tip to aid in mixing. Although many shapes and configurations of the device are contemplated to adequately mix the solutions, one preferred embodiment for the relative ease of manufacture and adequate mixing performance includes a cylindrical tip with about 5 to 10 turbulators centrally disposed within the tip and are stationary therein. The turbulators are rudder-like, and most preferably are segments of planar helix with the segments offset 180 degrees about the axis of helix-wrap from one another.

An additional mixing and delivery device combines the first and second mixtures or components in a device that is syringe-like in form. The two solutions are pre-measured and held in two chambers isolated from one another. A plunger connected with the chambers is used by an operator applying force to the plunger to push on the two solutions inside the two chambers simultaneously. The solutions are simultaneously delivered into a tip from one or more openings at the end of the chambers oppositely disposed to the plunger where mixing occurs. A plurality of turbulators is disposed within the tip such that the solutions are sloshed, agitated, and/or moved about the turbulators within the confines of the tip to aid in mixing. Although many shapes and configurations of the device are contemplated to adequately mix the solutions, one preferred embodiment for the relative ease of manufacture and adequate mixing performance, includes a cylindrical tip with about 5 to 10 turbulators centrally disposed within the tip and are stationary therein. The turbulators are rudder-like, and most preferably are segments of planar helix with the segments offset 180 degrees about the axis of helix-wrap from one another.

Figure 2:
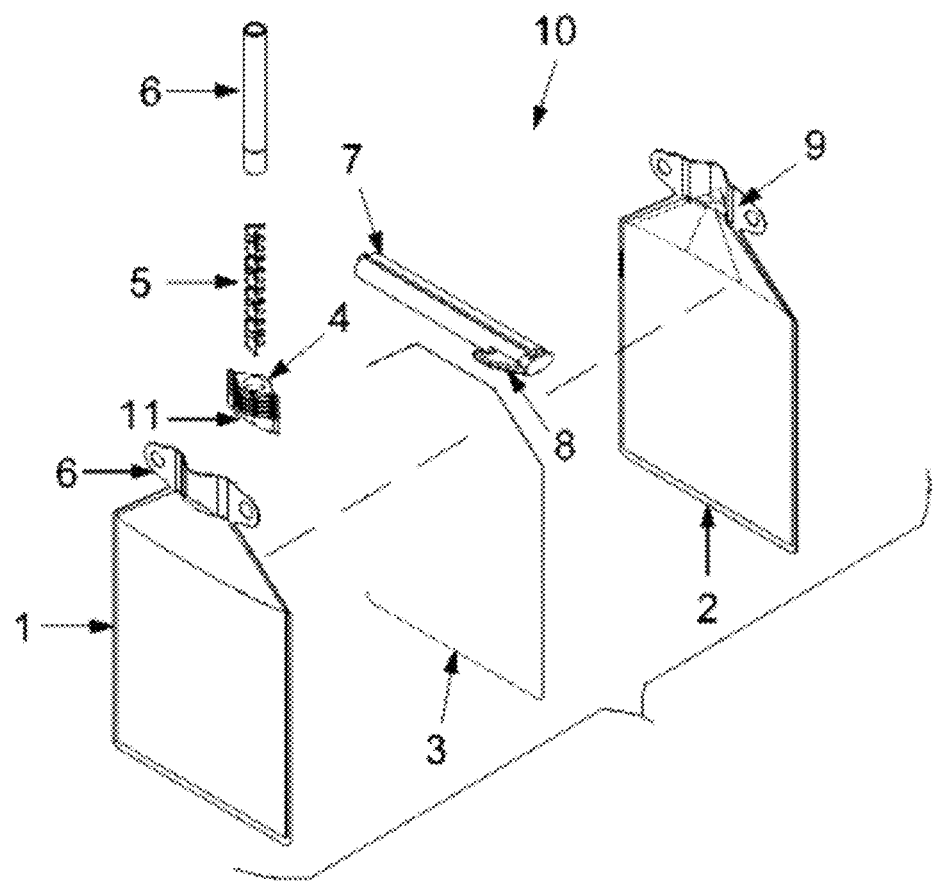
FIG. 2 is an exploded view of the delivery device of FIG. 1.

Referring to FIGS. 1 and 2, a preferred delivery device in accordance with the present disclosure is generally designated 10. Delivery device 10 includes a first side outer layer 1, a second side outer layer 2, a separator wall 3, a sealing and static mixer housing 4, a multi-turn helical mixing element 5, a mixer housing tube 6, a closure pinch clip 7, a pinch clip release feature 8, a gripping bracket 9, and a mixture component exit point 11.

First side outer layer 1, second side outer layer 2, and wall separator 3 are tapered on one end leading to an edge with a length less than that at the respective distal edges. First and second side outer layers 1 and 2 further include gripping brackets 9 formed as laterally flared portions at the tapered ends of the outer layers located at the tapered ends.

The first side outer layer 1, the second side outer layer 2, and the wall separator 3 are adhered jointly about their periphery on the left and right side edges and bottom edges distal to the tapered top edges with the wall separator 3 placed between layers 1 and 2. Thus, two substantially identical chambers are formed for holding, component A and component B, respectively, between first side layer 1 and wall separator 3, and between second side outer layer 2 and wall separator 3.

At the tapered edge, an exit point 11 for components A and B from their respective chambers, is formed. At exit point 11, a sealing and static mixer housing element 4 is placed and adhered to first side outer layer 1 and one side, and second side outer layer 2 on the opposite side.

A multi-turn mixing helical element 5 is placed centrally at the opening of static mixer housing element 4. The multi-turn mixing helical element 5 includes preferably 5 to 10 turbulators, which are segments of a planar helix offset 180 degrees about the longitudinal axis of the helix wrap from one another. Mixer housing tube 6 is a cylindrical tube which is slotted around multi-turn helical mixing element 5 with one opening end secured and sealed in the opening of the static mixer housing element 4.

Pinch clip 7 is preferably a bar bent approximately at half its length and doubled over itself. The bar is doubled over itself and the tapered edges of first side outer layer 1 and second side outer layer 2 and compacted or pinched and sealed against separator wall 3 internally in the device. The pinch clip 7 serves to seal the chambers formed for holding components A and B, respectively, between first side layer 1 and wall separator 3 and between second side outer layer 2 and wall separator 3 and impede the mixing of components A and B. The pinch clip 7 is released by pressing pinch clip release finger 8, which disengages the portions of the clip attached and locked together when folded over itself.

During operation, when the chambers for holding components A and B are filled according to the present disclosure and the pinch clip 7 is removed, physical force is used to press first side outer layer 1 and second side outer layer 2 towards one another and to force components A and B into the mixer mount housing 4. Force can be applied a number of ways, but in a preferred embodiment of the physical mixing process, the fingers of one hand of a user are placed at the gripping elements 9, and the fingers of a second hand of a user force the first and second outer layer sides 1 and 2 towards one another in a scrunching or gripping motion.

The combination continues through mixing element housing tube 6 and mixing is aided by flow about and around mixing helical mixing element 5. The combination exits the mixing element housing tube 6 at the end distal to the mixer mount housing element 4 and can be applied as a blockage agent.

When the adequately mixed combination exits the tip, it has the form of a nearly cured soft-solid polymeric matrix capable of temporarily, that is to say not permanently, adhering to a surface. In utility as a hemostasis product for controlling blood loss, the composition adheres and partially conforms to the site of bleeding, such as in or on a wound.

The weight and volume of the components of the compositions, along with the exact compounds used, relative to one another may vary and still produce a type of blockage, but certain ranges produce compositions with the most desired qualities including firmness, proportions of components reacted, and homogeneity.

The first mixture (component B) comprises a siloxane polymer, a surfactant, a catalyst-containing siloxane polymer, and a salt or compound of metals, or mixture of compounds of metals.

Preferably, the first mixture (component B) includes, by weight or volume, about 10%-100% polysiloxane, about 0%-25% surfactant, about 0%-25% catalyst, about 1%-30% compounds of metals.

Preferably, the second mixture (component A) contains, by weight or volume, about 10%-100% vinylpolymethysiloxane, about 0%-25% surfactant, and about 1%-20% hydrogen peroxide. Preferably, hydrogen peroxide is about 5-18%, and more preferably about 17.5%, by weight or volume of component A. The concentration of hydrogen peroxide is about 40%-100%, and preferably about 50%, by volume.

The second mixture, preferably, also contains about 0%-10% by weight or volume of particle fillers. Non-limiting examples of particle fillers in component A include metal compounds that include silicon oxide (1 nanometer to 10 micrometer size), fumed silica (1 nanometer to 10 micrometer size), titanium dioxide (1 nanometer to 10 micrometer size), diatomaceous earth (1 nanometer to 10 micrometer size), calcium silicate (1 nanometer to 10 micrometer in size), aluminum silicate (1 nanometer to 10 micrometer in size), zeolites (small pore, medium pore, large pore), mesoporous materials (1 nanometer to 5 micrometer in size), clays (1 nanometer to 10 micrometer in size), polyhedral oligomeric silsesquioxane (1 nanometer to 1 micrometer; trade name POSS® from Hybrid Plastics, Inc., Hattiesburg, Miss.), and chemical and functional derivatives of polyhedral oligomeric silsesquioxane (trade name POSS®). Particle fillers in component A can range from about 0%-10%, preferably about 0%-2%, by weight or volume.

It was observed during experimentation that approximately equal parts of the first and second mixtures generates a soft-solid matrix 2-10 times in volume depending upon the formulation. In use, with or without a delivery device, any volume of composition desired can be formed by using adequate amounts of the first and second mixtures.

The final polymeric product includes a hemostatic wound dressing that is especially intended for emergency use as an external temporary wound dressing to achieve hemostasis for moderate to severe bleeding. It includes of two solutions (component A and component B) that are kept separate until application and combination. It is delivered using a dual chamber hand-powered delivery device, which is preferably a single use, disposable device for simultaneously mixing and directing the delivery of the active hemostatic dressing into the wound. It is sterilized by gamma irradiation. The delivery syringe consists of a hand-powered, two-chambered delivery device equipped with a mixing nozzle. The delivery syringe is comprised of injection molded nylon and injection molded polypropylene.

To deliver the hemostatic wound dressing, the user removes the sealing cap and twists on the dispensing tube. The applicator nozzle is inserted into the base of wound opening. The press-on plungers are aligned with the dual tube. The user presses down to dispense, moving in a circular motion to the outer edges of the wound.

In a preferred embodiment, component "A" includes vinylpolymethysiloxane (a siloxane polymer), polyoxyethylene sorbitan monoleate (Polysorbate 80/Tween 80™, a surfactant), hydrogen peroxide and silicon oxide (fumed silica), and component "B" includes methylhydrosiloxane-dimethylsiloxane (a siloxane copolymer) in addition to vinylpolymethysiloxane (a siloxane polymer), polyoxyethylene sorbitan monooleate (Polysorbate 80/Tween 80™, a surfactant), platinum divinylpolymethylsiloxane (a catalyst-containing siloxane polymer), iron oxide, and calcium oxide.

Mechanism of Action

The hemostatic wound dressing is made at the point of use by combining the two mixtures (components A and components B). Adequate mixing of the two components is necessary to achieve the most desirable composition for the hemostatic agent. When the two components A and B combine, the curing agent in the component B is free to react with component A, with the aid of iron oxide and calcium oxide. The curing agent in component B, and the activating agent in component A act upon the siloxane polymers in both components A and B to form a soft solid matrix in less than 2 minutes. Curing is further enhanced by gentle warming during expansion in situ. Adequate mixing is facilitated by both micro-kinetic and mechanical mixing means. The micro-kinetic mixing means are carried out by the inclusion of fumed silica ($SiO_2$), food grade filler, in component A. Upon mixing, the fumed silica particles, via their abrasive qualities, act as local micro-stirrers which push, pull, carry, and intermingle the components of one of the solutions with the other as they comingle through the static mixing tip of the delivery device by which mechanical mixing is achieved. When delivered to the wound bed, the two components A and B interact with each other and expand rapidly, while forming the polymeric matrix that conforms to the inside of the wound creating a physical plug. This physical plug stops moderate to severe bleeding, initiating the body's natural clotting cascade. An occlusive bandage is place on top of the expanding polymeric matrix, to contain it within the wound space. The formulation is especially suited for use in emergency situations, including the battlefield. Once the patient has received medical attention, the hemostatic plug can be removed.

The rapid expansion of the formulation is achieved by the liberation of $O_2$, which swells the polymeric materials in a controlled manner. The $O_2$ is generated during controlled decomposition of $H_2O_2$, in conjunction with the oxides of calcium and iron in the polymeric matrix. Controlled ratios of CaO and $Fe_2O_3$ in component "B" initiate and moderate the reaction kinetics of $H_2O_2$ decomposition (component "A" contains the $H_2O_2$), modulating the rate of $O_2$ generation. $Fe_2O_3$ acts as an inhibitor to this spontaneous and exothermic reaction ($H_2O_2$ and CaO), and moderates the reactivity and heat of reaction. By controlling the reaction kinetics and decomposition of $H_2O_2$ to $O_2$, both reaction temperature and $O_2$ generation are regulated, thereby creating an optimum swelling/expansion of the cured polymeric semi-solid matrix. The reaction sequence may be summarized as follows:

$$CaO+Fe_2O_3+H_2O_2=O_2+H_2O+\text{mixed oxides of Ca}+\text{mixed oxides of Fe}+\text{Heat of reaction}\rightarrow \text{Components (A+B)}\rightarrow \text{FINAL PRODUCT}$$

The final Product is cross-linked and cured in about <300 seconds, and has a volume of expansion of approximately 150% to 800%. The heat generated during the decomposition of $H_2O_2$ serves two purposes: 1) It acts to speed up the cross-linking between the polymers and curing to form the resultant polymeric hemostatic product, as presented in FIG. 3; 2) Facilitate the combination for components A and B by decreasing the viscosity of the components as they combine in the mixing nozzle.

The surfactant, polyoxoethylene sorbitan monooleate (sold under the trade name Tween 80™), maintains the emulsion of Components A and B. It acts to reduce agglomeration and the resulting potential sedimentation of the components and consequently enhances the ability of the solutions to readily mix. The surfactant used in component, Tween 80™, is non-toxic, and has been used in other medical, food, and cosmetic products.

Iron oxide and calcium oxide both serve as reactants in the decomposition of hydrogen peroxide. Iron oxide acts as an inhibitor to the spontaneous reaction of the decomposition of $H_2O_2$ to $O_2$, and subsequent heat generation, serving as a rate-limiting step for the curing and firmness of the hemostatic wound dressing. This rate limiting step controls the heat generated from the interaction of hydrogen peroxide with oxides of calcium, and iron, keeping the hemostatic product with curing temperatures below 49° C., and in a typical 37° C. to 45° C.

Hydrogen peroxide is completely, or near completely, reacted upon combination of the two mixtures, and the final concentration of $H_2O_2$ in the hemostatic plug is 4% to 4.5%. The hydrogen peroxide does not have any chemical effect on the wound bed, rather, it is included to serve as a source of $O_2$, which is the component that causes the material to swell and fill the wound bed.

Once the components have reacted with each other, they form a semi-sold matrix that expands to completely fill the wound bed, physically restricting the outpour of blood or profuse bleeding from the wound, allowing the body to initiate blood's natural clotting cascade. The components A and B, and the product formed after mixing components A and B, do not have any chemical action on the wound bed.

EXAMPLES

Example 1

The following experiment was conducted to make a hydrogen peroxide containing polymeric solution and inorganic fillers containing polymeric solution. More specifically, the experiment involved use of a combination of inorganic fillers e.g., Group II (alkaline earth) and transition metal salts, and hydrogen peroxide containing polymeric solutions catalyzed by platinum polymer species for cross-linking of the polymeric matrices. The resultant is a cured, soft and firm polymer composite matrix with limited porosity.

Preparation of Two-Part System for Hemostatic Treatment for Slow, Mild and High Bleeding Using Controlled Mechanism The Gelest Encapsulant 41 Accelerated Cure system (bought from Gelest, Inc.). The viscosity (~4000 cSt) is optimized by adding several chemical ingredients and fillers to achieve adequate mixing in the deployment of the components to form the final product, a polymeric bandage material that will act as a hemostatic plug for low, medium and high bleeding from the lacerations and wounds. The main ingredients in the two-part Gelest Encapsulant 41 Accelerated Cure system were Optical Encapsulant Part A and Optical Encapsulant Part B, both obtained from Gelest, Inc.

Optical Encapsulant Part A contains:
(a) Poly(dimethylsiloxane), Vinyl Terminated: >70%
(b) Vinyl Modified Q Silica Resin: <30%
Optical Encapsulant Part B contains:
(a) Poly(dimethylsiloxane), Vinyl Terminated: >70%
(b) Vinyl Modified Q Silica Resin: <30%
(c) Methylhydrosiloxane-dimethylsiloxane Copolymer: <10%
Materials—Constituents and Suppliers:
(a) Vinyl Modified Q Silica Resin and Poly(dimethylsiloxane)-Vinyl Terminated (sold under the trade name Optical Encapsulant Part A)—Gelest, Inc. (Morrisville, Pa.)
(b) Vinyl Modified Q Silica Resin, Poly(dimethylsiloxane)-Vinyl Terminated and Methylhydrosiloxane-Dimethylsiloxane Copolymer (sold under the trade name Optical Encapsulant Part B)—Gelest, Inc. (Morrisville, Pa.)
(c) Pt-Divinyl Siloxane Catalyst—(a) Gelest, Inc. (Morrisville, Pa.) and (b) Johnson Matthey (West Deptford, N.J.)
(d) Calcium Oxide or CaO—(a) GFS Chemicals (Powell, Ohio), and (b) Mississippi Lime—Food Grade (St. Louis, Mo.)
(e) Iron oxide as $Fe_2O_3$—Alfa Aesar (Ward Hill, Mass.)

(f) Polyoxoethylene Sorbitan Monooleate/a.k.a. Tween 80—Alfa Aesar (Ward Hill, Mass.)
(g) 50% v/v Hydrogen Peroxide ($H_2O_2$)—Sigma Aldrich (St. Louis, Mo.)
(h) Fumed Silica ($SiO_2$)—Sigma Aldrich (St. Louis, Mo.)

The two polymeric solutions were classified into components A and B, which combine chemically to form cured and cross-linked polymeric foam that acts as an hemostatic bandage and plug to bleeding.

Component "A" comprised of a siloxane polymer, a surfactant, and hydrogen peroxide. The siloxane polymer is preferably vinylpolymethylsiloxane. The surfactant is preferably polyoxyethylene sorbitan monooleate (sold under trade name Polysorbate 80 or Tween 80™), and the hydrogen peroxide, preferably in a solution of 50% hydrogen peroxide ($H_2O_2$) and water, the hydrogen peroxide in Component "A" formulated to a concentration of 8.5%. Component "A" contains 81.4 wt % Optical Encapsulant Part B; 17.57 wt % hydrogen peroxide having a concentration of 50%; 0.90 wt % polyoxoethylene sorbitan monooleate; and 0.12 wt % fumed silica.

Component "B" comprised of a siloxane polymer, a surfactant, a catalyst-containing siloxane polymer, iron oxide, and an oxide or salt of a Group II element. The siloxane polymer is preferably vinylpolymethylsiloxane. The surfactant is preferably polyoxyethylene sorbitan monooleate (Tween 80™), the catalyst-containing siloxane polymer is preferably platinum divinylpolymethylsiloxane. The iron oxide is preferably $Fe_2O_3$, and the Group II element oxide is preferably CaO. Component "B" contains, 83.6 wt % Optical Encapsulant Part A; 12.93 wt % calcium oxide; 1.72% Platinum Divinylpolymethylsiloxane; 1.52 wt % iron oxide ($Fe_2O_3$); and, 0.23 wt % polyoxoethylene sorbitan monooleate.

TABLE 1

Component "A" Formulation (wt %)

| Fumed $SiO_2$ (Sigma) Fumed Silica Silicon Dioxide | Resin (Gelest) Optical Encapsulant Part B | Tween-80 (Alfa) polyoxoethylene sorbitan monooleate | 50% v/v $H_2O_2$ (Sigma) Hydrogen Peroxide |
|---|---|---|---|
| 0.12 wt % | 81.41 wt % | 0.90 wt % | 17.57 wt % |

TABLE 2

Component "B" Formulation (wt %)

| Catalyst (Gelest) Platinum-Divinyl-polymethyl siloxane | CaO (GFS) Calcium Oxide | $Fe_2O_3$ (Alfa) Iron Oxide | Resin (Gelest) Optical Encapsulant Part A | Tween-80 (Alfa) polyoxoethylene sorbitan monooleate |
|---|---|---|---|---|
| 1.72 wt % | 12.93 wt % | 1.52 wt % | 83.60 wt % | 0.23 wt % |

TABLE 3

Various Compositions of Component A for Testing

| Sample # | 50% $H_2O_2$ | Tween-80 | Resin (Gelest) Optical Encapsulant Part B | Total weight after mix |
|---|---|---|---|---|
| 3-1 | 1 g | 1 g | 5.67 g | 7.34 g |
| 3-2 | 1 g | 0.5 g | 5.67 g | 6.85 g |
| 3-3 | 1 g | 1 g | 5.0 g | 6.81 g |
| 3-4 | 1 g | 0.5 g | 5.0 g | 6.32 g |

Composition for Component B consisted of homogeneous mixing of 8.75 g Optical Encapsulant Part A, 1 g of Platinum-Divinylpolymethylsiloxane (hereafter, abbreviated as Pt-Siloxane), and 0.25 g of Manganese Dioxide ($MnO_2$). Mixing was carried out using a hand-held spatula for 1 minute to 10 minutes. The batch preparation was labeled as 3-5.

TABLE 4

Reaction Between Component A and Component B

| Sample # | Component A | Component B | Observations |
|---|---|---|---|
| 4-1 | 2 mL of sample 3-5 | 2 mL of sample 3-1 | 10 seconds mixing; reaction started by 30 seconds; ~6 X expansion in the next 40 seconds; curing temperature was warm |
| 4-2 | 2 mL of sample 3-5 | 2 mL of sample 3-2 | 10 seconds mixing; reaction started by 30 seconds; ~5.5 X expansion in the next 50 seconds; curing temperature was warm |
| 4-3 | 2 mL of sample 3-5 | 2 mL of sample 3-3 | 10 seconds mixing; reaction started by 30 seconds; ~6 X expansion in the next 40 seconds; curing temperature was warm |
| 4-4 | 2 mL of sample 3-5 | 2 mL of sample 3-4 | 10 seconds mixing; reaction started by 40 seconds; ~7.5 X expansion in the next 40 seconds; curing temperature was very warm |

Approximately equal parts of Component "A" (about 2 mL) and Component "B" (about 2 mL) were mixed vigorously in a plastic tube or container to obtain a homogeneous mixture with a total volume of 4 mL. Reaction between constituents of Component A and B resulted in a soft-solid matrix having a larger volume than the combined volume of Component A and Component B. The volume of the soft-solid matrix was about 16 to about 30 ml (Table 4; samples 4-1 to 4-4), which was about 4 to 7.5 times the combined volume (4 mL) of Component A and Component B. The results are presented in Table 4.

Example 2

The two polymeric solutions were classified into components A and B. Component "A" comprised of Optical Encapsulant Part B polymer, polyoxyethylene sorbitan mooleate (Tween 80™) surfactant, and hydrogen peroxide, a solution of 50% hydrogen peroxide ($H_2O_2$) and water.

TABLE 5

Various Compositions of Component A for Testing

| Sample # | 50% v/v $H_2O_2$ | Tween-80 | Optical Encapsulant Part B | Total weight after mixing |
|---|---|---|---|---|
| 5-1 | 1 g | 1 g | 5.67 g | 7.34 g |
| 5-2 | 1 g | 0.5 g | 5.67 g | 6.85 g |
| 5-3 | 1 g | 1 g | 5.0 g | 6.81 g |
| 5-4 | 1 g | 0.5 g | 5.0 g | 6.32 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, iron oxide ($Fe_3O_4$), and/or chitosan (Sigma-Aldrich, Mo.).

TABLE 6

Various Compositions of Component B for Testing

| Sample # | Iron Oxide $Fe_3O_4$ | Chitosan | Pt-Siloxane | Optical Encapsulant Part A | Total weight after mixing |
|---|---|---|---|---|---|
| 6-1 | 0.25 g | 0.5 g | 1 g | 8.75 g | 10.5 g |
| 6-2 | 0.25 g | 0.0 g | 1 g | 8.75 g | 10.0 g |

TABLE 7

Reaction Between Component A and Component B

| Sample # | Component A | Component B | Observations |
|---|---|---|---|
| 7-1 | 2 mL of sample 5-1 | 2 mL of sample 6-1 | 30 seconds mixing; reaction started by 30 seconds; gray solid mass obtained after 1 minute; ~2.5 X expansion after 5 minutes |
| 7-2 | 2 mL of sample 5-2 | 2 mL of sample 6-2 | 30 seconds mixing; reaction started by 2 minute; ~1.5 X expansion after 5 minutes |
| 7-3 | 2 mL of sample 5-3 | 2 mL of sample 6-2 | |
| 7-4 | 2 mL of sample 5-4 | 2 mL of sample 6-1 | 30 seconds mixing; reaction started by 1 minute; gelatinous mass obtained after 1 minute; ~3 X expansion after 5 minutes |

Approximately equal parts of Component "A" (about 2 mL) and Component "B" (about 2 mL) were mixed vigorously in a plastic tube or container to obtain a homogeneous mixture with a total volume of 4 mL. Reaction between constituents of Component A and Component B resulted in a gel or solid matrix with a slow reaction. The volume of the matrices was about 6 to about 12 ml (Table 7; samples 7-1 to 7-4), which was about 1.5 to 3 times the combined volume (4 mL) of Component A and Component B. The results are presented in Table 7.

Example 3

The two polymeric solutions were classified into components A and B. Component "A" comprised of Optical Encapsulant Part B polymer, polyoxyethylene sorbitan mooleate (Tween 80™) surfactant, and hydrogen peroxide, a solution of 50% hydrogen peroxide ($H_2O_2$) and water.

TABLE 8

Various Compositions of Component A for Testing

| Sample # | 50% v/v $H_2O_2$ | Tween-80 | Optical Encapsulant Part B | Total weight after mixing |
|---|---|---|---|---|
| 8-1 | 1 g | 1 g | 5.67 g | 7.34 g |
| 8-2 | 1 g | 0.5 g | 5.67 g | 6.85 g |
| 8-3 | 1 g | 1 g | 5.0 g | 6.81 g |
| 8-4 | 1 g | 0.5 g | 5.0 g | 6.32 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer and iron oxide ($Fe_3O_4$).

TABLE 9

Various Compositions of Component B for Testing

| Sample # | Iron Oxide $Fe_3O_4$ | Pt-Siloxane | Optical Encapsulant Part A | Total weight after mixing |
|---|---|---|---|---|
| 9-1 | 0.75 g | 2 g | 17.5 g | 20.25 g |
| 9-2 | 1.00 g | 2 g | 17.5 g | 20.50 g |
| 9-3 | 1.50 g | 2 g | 17.5 g | 21.00 g |

TABLE 10

Reaction Between Component A and Component B

| Sample # | Component A | Component B | Observations |
|---|---|---|---|
| 10-1 | 3.2 mL of sample 8-1 | 3.2 mL of sample 9-3 | 30 seconds mixing; reaction started by 90 seconds; ~2.5 X expansion after 3 minutes; 4 X expansion after 6 minutes |
| 10-2 | 2.7 mL of sample 8-2 | 2.8 mL of sample 9-3 | 60 seconds mixing; reaction started by 90 seconds; 4 X expansion after 6 minutes |
| 10-3 | 4.75 mL of sample 8-3 | 2.5 mL of sample 9-3 | 60 seconds mixing; reaction started by 90 seconds; ~2 X expansion after 1 minute; 3 X expansion after 5 minutes |
| 10-4 | 2.1 mL of sample 8-4 | 2.1 mL of sample 9-3 | 60 seconds mixing; reaction started by 90 seconds; ~2 X expansion after 1.5 minutes; 3 X expansion after 5 minutes |

Example 4

Chemical reactivity of 1 mL 50% v/v $H_2O_2$ with:
(a) 0.2 g FeO produced slow effervescence in 5 to 10 minutes
(b) 0.2 g $Ti_2O_3$ produced very slow effervescence after 30 minutes
(c) 0.2 g $MnO_2$ produced fast and instantaneous effervescence in 1 second
(d) 0.2 g $FeCl_2$ produced fast and instantaneous effervescence within 1 second
(e) 0.2 g $Fe_3O_4$ produced fairly rapid effervescence in 1 minute
(f) 0.2 g $TiO_2$ produced no effervescence (g) 0.2 g FeO+2(M) NaOH produced fast and instantaneous effervescence in 2 seconds (h) 0.1 g $Ti_2O_3$+0.1 g 2(M) NaOH produced fairly rapid effervescence in 1 minute (i) 0.2 g 2(M) NaOH produces no effervescence (j) 0.2 g CaO produced fast and instantaneous effervescence immediately (within 1 second)

(k) 0.1 g FeO+0.1 g CaO (1:1 weight ratio) produced fast and instantaneous effervescence immediately (within 3 seconds)

(l) 0.2 g MgO (20 nm particle size) produced fast and immediate effervescence after 5 seconds (m) 0.1 g FeO+0.1 g MgO (1:1 weight ratio) produced fast and instantaneous effervescence after 5 seconds Based on the above experiments, biological safety, cost effectiveness, ease of use and features such as biocompatibity and minimal toxicity for using the inorganic materials in the components A and/or B for making a hemostatic treatment, calcium oxide and iron oxides were prioritized to pursue further experiments.

Example 5

Based on the results from Example 5, calcium oxide (CaO), and combination of calcium oxide (CaO) and Iron oxide (FeO) were used in the following experiments. The two polymeric solutions were classified into components A and B.

Component "A" comprised of Optical Encapsulant Part B polymer, polyoxyethylene sorbitan mooleate (Tween 80™) surfactant, and hydrogen peroxide, a solution of 50% hydrogen peroxide ($H_2O_2$) and water.

TABLE 11

Various Compositions of Component A for Testing

| Sample # | 50% v/v $H_2O_2$ | Tween-80 | Optical Encapsulant Part B | Total weight after mixing |
|---|---|---|---|---|
| 11-1 | 5 g | 5 g | 25 g | 35 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, calcium oxide (CaO) and iron oxide (FeO). The contents were hand mixed using a spatula for 5 minutes that turned into a viscous, chocolate colored mixture. Another batch (sample 12-2) was made in a similar way without adding FeO in the composition, which turned into a viscous, milky white mixture.

TABLE 12

Various Compositions of Component B for Testing

| Sample # | FeO | CaO | Pt-Siloxane | Optical Encapsulant Part A | Total weight after mixing |
|---|---|---|---|---|---|
| 12-1 | 1 g | 1 g | 2 g | 16 g | 20 g |
| 12-2 | 0 g | 1 g | 1 g | 8 g | 10 g |

TABLE 13

Reaction between Component A and Component B

| Sample # | Component A | Component B | Observations |
|---|---|---|---|
| 13-1 | 5 mL of sample 11-1 | 5 mL of sample 12-1 | 20 seconds mixing; reaction started by 40 seconds; 4.5 X expansion after 3 minutes |
| 13-2 | 5 mL of sample 11-1 | 5 mL of sample 12-2 | 20 seconds mixing; reaction started by 40 seconds; 3 X expansion after 1 minute; 5 X expansion after 2 minutes |

Example 6

Combination of barium hydroxide, calcium oxide (CaO), and Iron oxide ($Fe_3O_4$) inorganic fillers were used in the following experiments. The two polymeric solutions were classified into components A and B.

Component "A" comprised of Optical Encapsulant Part B polymer, polyoxyethylene sorbitan mooleate (Tween 80™) surfactant, and hydrogen peroxide, a solution of 50% hydrogen peroxide ($H_2O_2$) and water.

TABLE 14

Various Compositions of Component A for Testing

| Sample # | 50% v/v $H_2O_2$ | Tween-80 | Optical Encapsulant Part B | Total weight after mixing |
|---|---|---|---|---|
| 14-1 | 5 g | 5 g | 25 g | 35 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, barium hydroxide, calcium oxide (CaO) and iron oxide ($Fe_3O_4$). The contents were hand mixed using a spatula for 5 minutes to a homogeneous mixture.

TABLE 15

Various Compositions of Component B for Testing

| Sample # | Barium hydroxide | CaO | $Fe_3O_4$ | Pt-Siloxane | Optical Encapsulant Part A | Total weight |
|---|---|---|---|---|---|---|
| 15-1 | 2 g | 1 g | 0 g | 1 g | 8 g | 12 g |
| 15-2 | 1 g | 1 g | 0 g | 1 g | 8 g | 11 g |
| 15-3 | 0.5 g | 1 g | 0.5 g | 1 g | 8 g | 11 g |

TABLE 16

Reaction Between Component A and Component B

| Sample # | Component A | Component B | Observations |
|---|---|---|---|
| 16-1 | 5 mL of sample 14-1 | 5 mL of sample 15-1 | 20 seconds mixing; formed soft, solid gel in 1 minute; 1.5 X expansion after 3 minutes |
| 16-2 | 5 mL of sample 14-1 | 5 mL of sample 15-2 | 20 seconds mixing; reaction started by 30 seconds; solid white gel; no expansion after 5 minutes |
| 16-3 | 5 mL of sample 14-1 | 5 mL of sample 15-3 | 20 seconds mixing; reaction started by 60 seconds; solid white gel; 2 X expansion after 2 minutes |

Example 7

Calcium oxide (CaO) as an inorganic filler was used in the following experiments. The two polymeric solutions were classified into components A and B.

Component "A" comprised of Optical Encapsulant Part B polymer, polyoxyethylene sorbitan mooleate (Tween 80™) surfactant, and hydrogen peroxide, a solution of 50% v/v hydrogen peroxide ($H_2O_2$) and water.

TABLE 17

Various Compositions of Component A for Testing

| Sample # | 50% v/v $H_2O_2$ | Tween-80 | Optical Encapsulant Part B | Total weight after mixing |
|---|---|---|---|---|
| 17-1 | 6 g | 3 g | 23 g | 32 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, and calcium oxide (CaO). The contents were hand mixed using a spatula for 5 minutes to a homogeneous mixture.

TABLE 18

Various Compositions of Component B for Testing

| Sample # | CaO | Pt-Siloxane | Optical Encapsulant Part A | Total weight |
|---|---|---|---|---|
| 18-1 | 1.5 g | 1 g | 7 g | 9.5 g |
| 18-2 | 6 g | 4 g | 28 g | 38 g |

TABLE 19

Reaction between Component A and Component B

| Sample # | Component A | Component B | Observations |
|---|---|---|---|
| 19-1 | 5 mL of sample 17-1 | 5 mL of sample 18-1 | 15 seconds mixing; reaction started in 10 seconds; 5 X expansion within 30-40 seconds |
| 19-2 | 25 mL of sample 17-1 | 25 mL of sample 18-2 | 15 seconds mixing; reaction started in 10 seconds; 6 X expansion within 40 seconds |

Example 8

Calcium oxide (CaO), Iron oxide ($Fe_3O_4$) and clay (Montmorillonite, PGW from Nanocor, Inc.) were used as inorganic fillers in the following experiments. The two polymeric solutions were classified into components A and B. Fresh beef blood used for the experiment was obtained from local butcher (Merrifield, Va.).

Component "A" comprised of Optical Encapsulant Part B polymer, polyoxyethylene sorbitan mooleate (Tween 80™) surfactant, montmorillonite clay (PGW) and hydrogen peroxide, a solution of 50% v/v hydrogen peroxide ($H_2O_2$) and water.

TABLE 20

Various Compositions of Component A for Testing

| Sample # | 50% v/v $H_2O_2$ | Tween-80 | PGW Clay | Optical Encapsulant Part B | Total weight after mixing |
|---|---|---|---|---|---|
| 20-1 | 6 g | 1.5 g | 2 g | 22 g | 31.5 g |
| 20-2 | 6 g | 1.5 g | 1.5 g | 22 g | 31.0 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, montmorillonite clay (PGW), calcium oxide (CaO) and iron oxide ($Fe_3O_4$). The contents were hand mixed using a spatula for 5 minutes to a homogeneous mixture.

TABLE 21

Various Compositions of Component B for Testing

| Sample # | CaO | $Fe_3O_4$ | PGW Clay | Pt-Siloxane | Optical Encapsulant Part A | Total weight |
|---|---|---|---|---|---|---|
| 21-1 | 3 g | 1 g | 0 g | 3 g | 26 g | 33 g |
| 21-2 | 3 g | 1 g | 0.5 g | 3 g | 26 g | 33.5 g |

TABLE 22

Reaction Between Component A and Component B

| Sample # | Component A | Component B | Blood | Observations |
|---|---|---|---|---|
| 22-1 | 5 mL of sample 20-1 | 5 mL of sample 21-1 | 0 g | 15 seconds mixing; reaction started in 60 seconds; 1.5 X expansion within 90 seconds |
| 22-2 | 5 mL of sample 20-2 | 5 mL of sample 21-2 | 23 g | 15 seconds mixing; reaction started in 15 seconds; 4 X expansion within 40 seconds; product is solid polymeric foam matrix |
| 22-3 | 4 mL of sample 20-2 | 4 mL of sample 21-2 | 40 g | 15 seconds mixing; reaction started in 10 seconds; 4 X expansion within 40 seconds; product is solid polymeric foam matrix |

Example 9

The main aim of this experiment was to study the effect of the catalyst, platinum divinylpolymethylsiloxane (termed as Pt-Siloxane) in the curing and cross-linking effect of the polymeric mixtures when two components (A and B) are mixed together. The curing parameters comprised of time and firmness of the firm polymeric foamy matrix thus formed at the end of the reaction. Calcium oxide (CaO), Iron oxide ($Fe_3O_4$) and clay (Montmorillonite, PGW from Nanocor, Inc.) were used as inorganic fillers in the following experiments. The two polymeric solutions were classified into components A and B.

Component "A" comprised of Optical Encapsulant Part B polymer, polyoxyethylene sorbitan mooleate (Tween 80™)

surfactant, fumed silica ($SiO_2$) and hydrogen peroxide, a solution of 50% v/v hydrogen peroxide ($H_2O_2$) and water.

TABLE 23

Various Compositions of Component A for Testing

| Sample # | 50% v/v $H_2O_2$ | Tween-80 | $SiO_2$ | Optical Encapsulant Part B | Total weight after mixing |
|---|---|---|---|---|---|
| 23-1 | 7.5 g | 1.875 g | 0.5 g | 27.5 g | 31.5 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, calcium oxide (CaO) and iron oxide ($Fe_3O_4$). The contents were hand mixed using a spatula for 5 minutes to a homogeneous mixture.

TABLE 24

Various Compositions of Component B for Testing

| Sample # | CaO | $Fe_3O_4$ | Pt-Siloxane | Optical Encapsulant Part A | Total weight |
|---|---|---|---|---|---|
| 24-1 | 0.875 g | 0.125 g | 0.125 g | 6.5 g | 7.625 g |
| 24-2 | 3 g | 1 g | 0 g | 6.5 g | 7.5 g |

TABLE 25

Reaction between Component A and Component B

| Sample # | Component A | Component B | Observations |
|---|---|---|---|
| 25-1 | 3 mL of sample 23-1 | 3 mL of sample 24-1 | 15 seconds mixing; 4 X and 4.5 X expansions within 75 and 120 seconds respectively; product is solid polymeric foam |
| 25-2 | 3 mL of sample 23-2 | 3 v of sample 24-2 | 15 seconds mixing; reaction starts in 15 seconds; 5.25 X expansion in 90 seconds; product is fluid gel, polymeric foam with bubbles |

Example 10

The main aim of this experiment was to study the effect of Calcium oxide (CaO) and Iron oxide ($Fe_2O_3$), used as inorganic fillers in the following experiments. The two polymeric solutions were classified into components A and B. Contents of the components A and B were mixed for 1-2 hours in a 5 quart mechanical mixer (Kitchen Aid brand). The mixing speed was varied between 200 rpm to 600 rpm to blend the contents together to obtain nice homogeneity of the final mixtures.

Component "A" comprised of Optical Encapsulant Part B polymer, polyoxyethylene sorbitan mooleate (Tween 80™) surfactant, diatomaceous earth (obtained from Sigma-Aldrich, Mo.), fumed silica ($SiO_2$) and hydrogen peroxide, a solution of 50% v/v hydrogen peroxide ($H_2O_2$) and water. The contents were mixed for 60 minutes at 100-300 rpm in a 5 quart Kitchen Aid mixer to obtain a homogeneous mixture.

TABLE 26

Various Compositions of Component A for Testing

| Sample # | 50% v/v $H_2O_2$ | Tween-80 | $SiO_2$ | Diatomaceous Earth | Optical Encapsulant Part B | Total weight |
|---|---|---|---|---|---|---|
| 26-1 | 175 g | 9 g | 1 g | 0.2 g | 811 g | 996.2 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, calcium oxide (CaO) and iron oxide ($Fe_2O_3$). The contents were mixed for 90 minutes at 100-300 rpm in a 5 quart Kitchen Aid mixer to obtain a homogeneous mixture.

TABLE 27

Various Compositions of Component B for Testing

| Sample # | CaO | $Fe_2O_3$ | Tween-80 | Pt-Siloxane | Optical Encapsulant Part A | Total weight |
|---|---|---|---|---|---|---|
| 27-1 | 128 g | 15 g | 2.25 g | 20 g | 850 g | 1013.0 g |
| 27-2 | 2.56 g | 0 g | 0.045 g | 0.4 g | 17 g | 20.005 g |
| 27-3 | 1.28 g | 0 g | 0.045 g | 0.4 g | 17 g | 18.725 g |

TABLE 28

Reaction Between Component A and Component B

| Sample # | Component A | Component B | Observations |
|---|---|---|---|
| 28-1 | 5 mL of sample 26-1 | 5 mL of sample 27-1 | 15 seconds mixing; 5 X expansion within 45 seconds; product is red colored solid, polymeric, spongy foam |
| 28-2 | 5 mL of sample 26-1 | 5 mL of sample 27-2 | 15 seconds mixing; 6 X expansion within 35 seconds; product is white colored solid, polymeric, firm foam |
| 28-3 | 5 mL of sample 26-1 | 5 mL of sample 27-3 | 15 seconds mixing; reaction starts after 90 seconds, 4.75 X expansion within 120 seconds; product is white colored solid, polymeric, firm foam |

Example 11

The main aim of this experiment was to study the effect of Potato starch (procured from local store: Safeway, Falls Church, Va.) present in component A, and its interaction with the polymeric mixture in component B. The two polymeric solutions were classified into components A and B. Contents of the components A and B were hand mixed for 15 minutes using spatula to obtain a homogeneous mixture.

Component "A" comprised of Optical Encapsulant Part B polymer, polyoxyethylene sorbitan mooleate (Tween 80™) surfactant, potato starch, and hydrogen peroxide, a solution of 50% v/v hydrogen peroxide ($H_2O_2$) and water. The contents were mixed for 15 minutes using a spatula to obtain a homogeneous mixture.

TABLE 29

Various Compositions of Component A for Testing

| Sample # | 50% v/v $H_2O_2$ | Tween-80 | Potato Starch | Optical Encapsulant Part B | Total weight |
|---|---|---|---|---|---|
| 29-1 | 2.16 g | 0.1 g | 0.1 g | 10 g | 12.36 g |
| 29-2 | 2.16 g | 0 g | 0.2 g | 10 g | 12.36 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, calcium oxide (CaO) and iron oxide ($Fe_2O_3$). The contents were mixed for 90 minutes at 100-300 rpm in a 5 quart Kitchen Aid mixer to obtain a homogeneous mixture.

TABLE 30

Various Compositions of Component B for Testing

| Sample # | CaO | $Fe_2O_3$ | Tween 80 | Pt-Siloxane | Optical Encapsulant Part A | Total weight |
|---|---|---|---|---|---|---|
| 30-1 | 1.505 g | 0.176 g | 0.026 g | 0.4 g | 10 g | 12.107 g |

TABLE 31

Reaction Between Component A and Component B

| Sample # | Component A | Component B | Observations |
|---|---|---|---|
| 31-1 | 5 mL of sample 29-1 | 5 mL of sample 30-1 | 15 seconds mixing; No expansion observed in 120 seconds; cured polymeric product in 5 minutes |
| 31-2 | 5 mL of sample 29-2 | 5 mL of sample 30-1 | 15 seconds mixing; No expansion observed in 60 seconds; cured polymeric product in 3 minutes |

Example 12

The main aim of this experiment was to synthesize large scale batches of components A and B, and study the expansion rates when components A and B are mixed together. The two polymeric solutions, classified into components A and B, were mechanically mixed for 2 hours in a Kitchen Aid mixer at 100 to 300 rpm to obtain homogeneous mixtures.

Component "A" comprised of Optical Encapsulant Part B polymer, polyoxyethylene sorbitan mooleate (Tween 80™) surfactant, fumed silica ($SiO_2$), and hydrogen peroxide, a solution of 50% v/v hydrogen peroxide ($H_2O_2$) and water. The contents were mixed for 90 minutes using a Kitchen Aid mixer at 200 rpm to obtain a homogeneous mixture.

TABLE 32

Various Compositions of Component A for Testing

| Sample # | 50% v/v $H_2O_2$ | Tween-80 | Fumed Silica | Optical Encapsulant Part B | Total weight |
|---|---|---|---|---|---|
| 32-1 | 175 g | 9 g | 1.2 g | 811 g | 12.36 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, calcium oxide (CaO) and iron oxide ($Fe_2O_3$). The contents were mixed for 120 minutes at 100 rpm in a 5 quart Kitchen Aid mixer to obtain a homogeneous mixture.

TABLE 33

Various Compositions of Component B for Testing

| Sample # | CaO | $Fe_2O_3$ | Tween 80 | Pt-Siloxane | Optical Encapsulant Part A | Total weight |
|---|---|---|---|---|---|---|
| 33-1 | 8.2 g | 0.15 g | 0.45 g | 0.95 g | 90.3 g | 12.107 g |

TABLE 34

Reaction Between Component A and Component B

| Sample # | Component A | Component B | Observations |
|---|---|---|---|
| 34-1 | 5 mL of sample 29-1 | 5 mL of sample 30-1 | 15 seconds mixing; Reaction begins within 40 seconds; 1.5 X, 3 X, 5.2 X in 60, 90 and 120 seconds respectively; cured polymeric foam in 2 minutes |

Example 13

The main aim of this experiment was to synthesize large scale batches of components A and B, and study the expansion rates when components A and B are mixed together. The two polymeric solutions, classified into components A and B, were mechanically mixed for 2 hours in a Kitchen Aid mixer at 100 to 300 rpm to obtain homogeneous mixtures.

Component "A" comprised of Optical Encapsulant Part B polymer, polyoxyethylene sorbitan mooleate (Tween 80™) surfactant, fumed silica ($SiO_2$), and hydrogen peroxide, a solution of 50% v/v hydrogen peroxide ($H_2O_2$) and water. The contents were mixed for 90 minutes using a Kitchen Aid mixer at 200 rpm to obtain a homogeneous mixture.

TABLE 35

Various Compositions of Component A for Testing

| Sample # | 50% v/v $H_2O_2$ | Tween-80 | Fumed Silica | Optical Encapsulant Part B |
|---|---|---|---|---|
| 35-1 | 131.4 g | 6.75 g | 4 g | 606.7 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, calcium oxide (CaO) and iron oxide ($Fe_2O_3$). The contents were mixed for 120 minutes at 100 rpm in a 5 quart Kitchen Aid mixer to obtain a homogeneous mixture.

TABLE 36

Various Compositions of Component B for Testing

| Sample # | CaO | $Fe_2O_3$ | Tween 80 | Pt-Siloxane | Optical Encapsulant Part A |
|---|---|---|---|---|---|
| 36-1 | 64.1 g | 7.4 g | 1.1 g | 9.9 g | 418.6 g |
| 36-2 | 70.5 | 0 g | 2.2 g | 9.9 g | 417.5 g |
| 36-3 | 94.5 | 11.1 g | 1.65 | 12.6 g | 610.6 |

TABLE 37

Reaction between Component A and Component B

| Sample # | Component A | Component B | Observations |
|---|---|---|---|
| 37-1 | 5 mL of sample 35-1 | 5 mL of sample 36-1 | 15 seconds mixing; Reaction begins within 40 seconds; 2.5 X in 160 seconds; cured, hard polymeric rubber in 2 minutes |
| 37-2 | 5 mL of sample 35-1 | 5 mL of sample 36-2 | 15 seconds mixing; Reaction begins within 40 seconds; 3.5 X in 160 seconds; cured, hard polymeric rubber in 2 minutes |
| 37-3 | 5 mL of sample 35-1 | 5 mL of sample 36-3 | 15 seconds mixing; Reaction begins within 10 seconds; 4 X in 35 seconds; cured polymeric foam in 2 minutes |

Example 14

The main aim of this experiment was to add calcium silicate ($CaSiO_3$) as an inorganic filler instead of fumed silica in the component A, and study the effect of curing when component A containing calcium silicate is mixed with component B in suitable ratios. The two polymeric solutions, classified into components A and B, were hand mixed for 15 minutes using a spatula to obtain homogeneous mixtures.

Component "A" comprised of Optical Encapsulant Part B polymer, polyoxyethylene sorbitan mooleate (Tween 80™) surfactant, calcium silicate (two grades: Vanisil HR 325 and Vanisil W-50 (procured from R. T. Vanderbilt Company, Inc., Norwalk, Conn.), and hydrogen peroxide, a solution of 50% v/v hydrogen peroxide ($H_2O_2$) and water. The contents were mixed for 90 minutes using a Kitchen Aid mixer at 200 rpm to obtain a homogeneous mixture.

TABLE 38

Various Compositions of Component A for Testing

| Sample # | 50% v/v $H_2O_2$ | Tween-80 | HR 325 $CaSiO_3$ | W 50 $CaSiO_3$ | Optical Encapsulant Part B |
|---|---|---|---|---|---|
| 38-1 | 2.64 g | 0.135 g | 0.018 g | 0 g | 12.2 g |
| 38-2 | 2.64 g | 0.135 g | 0.108 g | 0 g | 12.2 g |
| 38-3 | 2.64 g | 0.135 g | 0.144 g | 0 g | 12.2 g |
| 38-4 | 2.64 g | 0.135 g | 0 g | 0.108 g | 12.2 g |
| 38-5 | 2.64 g | 0.135 g | 0 g | 0.144 g | 12.2 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, calcium oxide (CaO) and iron oxide ($Fe_2O_3$). The contents were mixed for 120 minutes at 100 rpm in a 5 quart Kitchen Aid mixer to obtain a homogeneous mixture.

TABLE 39

Various Compositions of Component B for Testing

| Sample # | CaO | $Fe_2O_3$ | Tween 80 | Pt-Siloxane | Optical Encapsulant Part A |
|---|---|---|---|---|---|
| 39-1 | 10.1 g | 0.25 g | 0.176 g | 0.95 g | 67 g |

TABLE 40

Reaction Between Composition A and Composition B

| Sample # | Component A | Component B | Observations |
|---|---|---|---|
| 40-1 | 5 mL of sample 35-1 | 5 mL of sample 36-1 | 15 seconds mixing; 4.5 X expansion in 60 seconds; cured polymeric foam in 2 minutes |
| 40-2 | 5 mL of sample 35-2 | 5 mL of sample 36-1 | 15 seconds mixing; 5 X expansion in 90 seconds; cured polymeric foam in 2 minutes |
| 40-3 | 5 mL of sample 35-3 | 5 mL of sample 36-1 | 15 seconds mixing; 5 X expansion in 90 seconds; cured polymeric foam in 2 minutes |
| 40-4 | 5 mL of sample 35-4 | 5 mL of sample 36-1 | 15 seconds mixing; 4 X expansion in 90 seconds; cured polymeric foam in 2 minutes |
| 40-5 | 5 mL of sample 35-4 | 5 mL of sample 36-1 | 15 seconds mixing; 4.5 X expansion in 90 seconds; cured polymeric foam in 2 minutes |

Example 15

Measuring the Expansion Reactivity

Figure 4A:
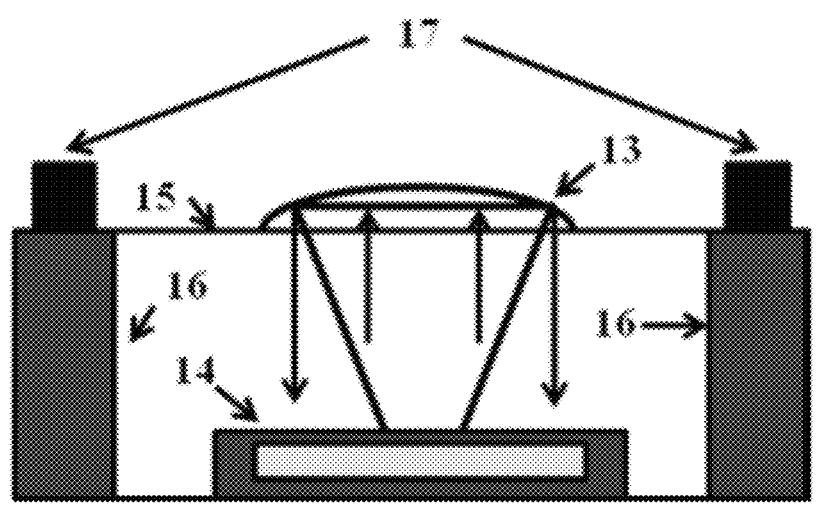
FIG. 4(a) is a schematic front view of a device for measuring the expansion reactivity of components A and B.
Figure 4B:
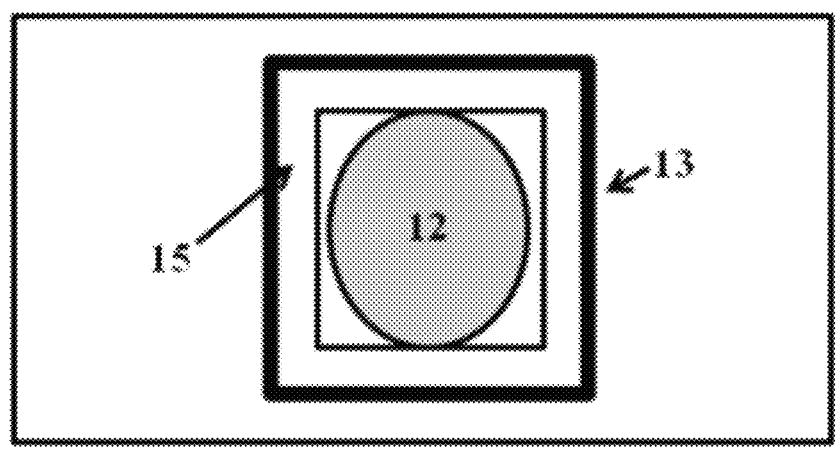
FIG. 4(b) is a schematic top view of the device of FIG. 4(a)

The expansion of the polymeric matrices is the essential component to achieving hemostasis within the wound. A standard apparatus has been developed and employed to test the unique expansion characteristics of final product formed by reacting and cross-linking components A and B. It is illustrated below with an explanation of its functionality in FIGS. 4(a) and 4(b).

Pressure Measurement

The downward pressure was measured using a standard lab scale (maximum weight of 3 kg) to measure the increased weight produced from the product formed from components A and B, and expanding against a standard hydrogel cover (which delivers pressure downward through a mock wound site). A 266 mL plastic cup (container) was used as a mock wound site for the experiments. This was chosen as a mock wound site because the cup has a fixed volume (266 mL) and a fixed base area (0.00238 $m^2$) through which the pressure is distributed. The pressure was determined by taking the increased weight (in kilogram), dividing that by the area (yielding kilogram per square meter), and then converting to Pa (Pascal; 1 Pascal=1 kilogram per square meter per square second). To simulate skin, a cardboard mat with a 5"×5" square cut in the middle (to allow for injection of the components A and B into the cup). This mat was supported on four legs to raise the height of the mat to just below the lip of the cup (approximately 2 mm of the cup above the mat). The mat was weighed down to prevent the expansion from lifting the apparatus. For a visual image of the apparatus, see the FIG. 4 (a) and FIG. 4 (b).

Front and top views of the apparatus as presented in FIGS. 4 (a) and (b): The hemostatic preparation is injected into the plastic tumbler (12), where it expands against the hydrogel wound cover (13). In response to the expansion of the product, the hydrogel generates a downward pressure, which is exerted through the base of the plastic tumbler and onto the Scale (14), which measures the pressure generated in grams. The hydrogel wound cover adheres to the cardboard support mat (15), which is in turn supported by four legs (16) to elevate the mat to the level of the polymeric product sample cup. A 5" square opening was cut into the mat to allow the cup to come through the top of the mat. The mat is weighed down by two weights (17), so that it is not moved by the expansion.

Experimental Procedure

The experiments were carried out by deliveries of two dual-tube cartridges into the sample cup, on a tarred scale. Each cartridge carrying 20 mL of the component "A" and 20 mL of component "B" of the polymeric product (80 mL total injection from 2 sets of cartridges). 80 mL of total components delivery was chosen to simulate the amount of polymeric product required for heavy bleed porcine tests. The weight of the delivered material was read off the tarred scale. The hydrogel cover bandage was placed over top of the cup and mat so that it adhered to both the cup lip and the mat surface. Once the hydrogel was in place, the scale was tarred to zero and the timer was started. Weight readings off the scale, were taken every 15 to 30 seconds, and a record was made of the time at which the expanding polymeric product foam made contact with the hydrogel.

Expansion Pressure Experiments

Three observations and validation trials were conducted to test and verify the proper operation of the test apparatus. These initial tests, found that the pressure generated by the expanding polymer composite matrix was causing a deflection in the support mat onto which the hydrogel was mounted, leading to lower pressure readings than the expanding polymeric composite was capable of generating. A greater weight was applied to the hydrogel mounting mat to ensure an accurate total pressure reading for the expanding cured polymeric product.

TABLE 41

| Trial # | Product delivered | Time (sec) | Weight on scale (g) | Pressure (Pascal) |
|---|---|---|---|---|
| 1 | 61.95 g | 0 | Tare at zero | 1136.47 |
|  |  | 15 | 276 | 4611.76 |
|  |  | 30 | 1120 | 3644.12 |
|  |  | 60 | 885 | 2660.00 |
|  |  | 90 | 646 | 2495.29 |
|  |  | 120 | 606 | 2392.35 |
|  |  | 150 | 581 | 2322.35 |
|  |  | 180 | 564 | 2281.18 |
| 1 | 61.95 g | 210 | 554 | 2240.00 |
|  |  | 240 | 544 | 2207.06 |
|  |  | 270 | 536 | 2182.35 |
|  |  | 300 | 530 | 2157.65 |
|  |  | 330 | 524 | 2145.29 |
|  |  | 360 | 521 | 2124.71 |
|  |  | 390 | 516 | 2112.35 |
|  |  | 420 | 513 | 1136.47 |

TABLE 42

| Trial # | Product delivered | Time (sec) | Weight on scale (g) | Pressure (Pascal) |
|---|---|---|---|---|
| 2 | 66.25 g | 15 | 40 | 164.71 |
|  |  | 30 | 1326 | 5460.00 |
|  |  | 45 | 842 | 3467.06 |
|  |  | 60 | 634 | 2610.59 |
|  |  | 90 | 514 | 2116.47 |
|  |  | 120 | 400 | 1647.06 |
|  |  | 150 | 365 | 1502.94 |
|  |  | 180 | 344 | 1416.47 |
|  |  | 210 | 332 | 1367.06 |
|  |  | 240 | 321 | 1321.76 |

TABLE 43

| Trial # | Product delivered | Time (sec) | Weight on scale (g) | Pressure (Pascal) |
|---|---|---|---|---|
| 3 | 65.05 g | 5 | 981 | 4039.41 |
|  |  | 15 | 1853 | 7630 |
|  |  | 30 | 2426 | 9989.41 |
|  |  | 60 | 1945 | 8008.82 |
|  |  | 90 | 1158 | 4768.24 |
|  |  | 120 | 1053 | 4335.88 |
|  |  | 150 | 888 | 3656.47 |
|  |  | 180 | 848 | 3491.76 |
|  |  | 210 | 690 | 2841.18 |
|  |  | 240 | 672 | 2767.06 |

Figure 5:
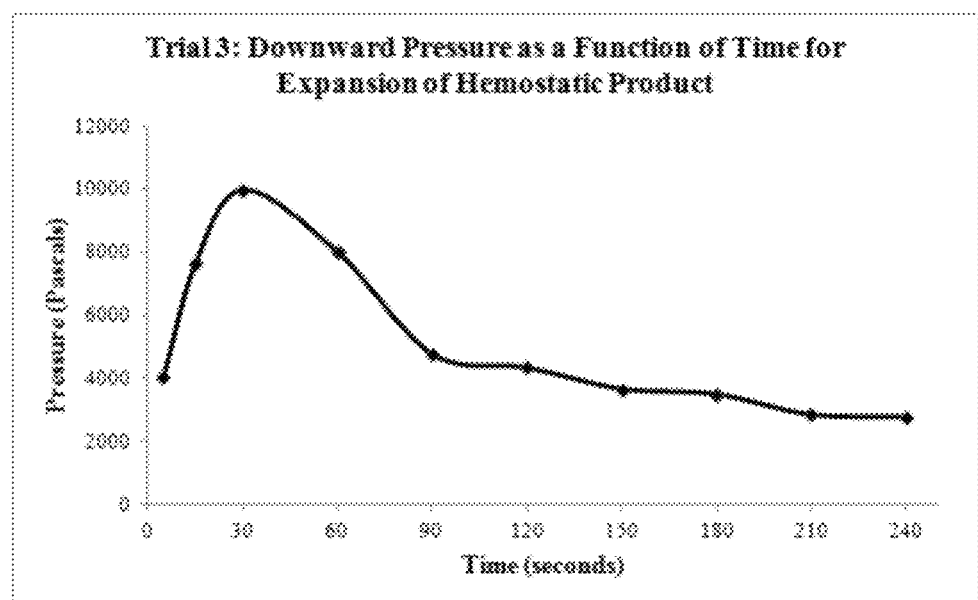
FIG. 5 is a graphical illustration of downward pressure measured as a function of time for expansion of the hemostatic polymer product.

For Trial #3, 65.05 g of the polyemric hemostatic composite material was dispensed into the sample cup. As noted, this trial employed heavier static weights to minimize the flexing of the Hydrogel support mat. Using this method, the maximum pressure observed was ~9990 Pa at 30 seconds. The expanding polymeric sample mass made contact with the hydrogel at approximately 4 seconds into timing (about 60 seconds after delivery). Results for the pressure generated by the expanding polymeric matrix versus time are shown in FIG. 5.

Example 16

The main aim of this experiment was to synthesize large scale batches of components A and B, and study the expansion rates when components A and B are mixed together. The two polymeric solutions, classified into components A and B, were mechanically mixed for 2 hours in a Kitchen Aid mixer at 100 to 300 rpm to obtain homogeneous mixtures.

Component "A" comprised of Optical Encapsulant Part B polymer, polyoxyethylene sorbitan mooleate (Tween 80™) surfactant, fumed silica ($SiO_2$), and hydrogen peroxide, a solution of 50% v/v hydrogen peroxide ($H_2O_2$) and water. The contents were mixed for 90 minutes using a Kitchen Aid mixer at 200 rpm to obtain a homogeneous mixture.

TABLE 44

Various Compositions of Component A for Testing

| Sample # | 50% v/v $H_2O_2$ | Tween-80 | Fumed Silica | Optical Encapsulant Part B | Total weight |
|---|---|---|---|---|---|
| 44-1 | 350.8 g | 18 g | 10.6 g | 1620.4 g | 12.36 g |

Component "B" comprised of Optical Encapsulant Part A polymer, polyoxyethylene sorbitan monooleate (Tween 80™) surfactant, platinum divinylpolymethylsiloxane (termed as Pt-Siloxane) as catalyst polymer, calcium oxide (CaO) and iron oxide ($Fe_2O_3$). The contents were mixed for 120 minutes at 100 rpm in a 5 quart Kitchen Aid mixer to obtain a homogeneous mixture.

TABLE 45

Various Compositions of Component B for Testing

| Sample # | CaO | $Fe_2O_3$ | Tween 80 | Pt-Siloxane | Optical Encapsulant Part A | Total weight |
|---|---|---|---|---|---|---|
| 45-1 | 259 g | 30.4 g | 4.6 g | 34.4 g | 1672 g | 12.107 g |

TABLE 46

Viscosities of Composition A at Different Temperatures

| Sample # | Temperature (degree C.) | cP (centi Poise) | RPM | Torque |
|---|---|---|---|---|
| 46-1 | 24.9 | 1766-1905 | 5 | 8.5% |
|  | 4.9 | 3671-3691 |  | 18.4% |
|  | 25.1 | 1776-1786 | 10 | 30.4% |
|  | 5.1 | 3036-3046 |  | 29.1% |
|  | 25.2 | 1766-1791 | 20 | 49.1% |
|  | 5.3 | 2952-3180 |  | 59.6% |

TABLE 47

Viscosities of Composition B at Different Temperatures

| Sample # | Temperature (degree C.) | Viscosity, cP (centi Poise) | RPM (Rotations per minute) | Torque |
|---|---|---|---|---|
| 47-1 | 25.8 | 2242-2262 | 5 | 11.4% |
|  | 4.9 | 4266-4286 |  | 21.6% |
|  | 25.9 | 1151-1191 | 10 | 11.8% |
|  | 5.1 | 4146-4157 |  | 42.9% |
|  | 26.1 | 610-600 | 20 | 16.2% |
|  | 5.3 | 4098-4103 |  | 82.7% |

Example 17

Durometer scale reading is one of the several procedures to measure the hardness of materials. Since our cured polymeric product is a firm foam matrix, and has similar physical properties to foam and/or rubber, such as stretchability, elongation etc. hardness tests for the polymeric product formed from components A and B were carried out. 20 mL sample 44-1 and 20 mL sample 45-1 were placed in a dual-cartridge syringe and released in a 50 mL plastic centrifuge tube. After waiting for 5 minutes for polymeric product to complete expanding due to chemical interactions between components A and B in the tube, the polymeric composite product is taken out. This was followed by an incision of the curved expanded polymeric product to make it a flat surface or base. The durometer (Brand: Rex Durometer; Model#: 1600) was put on the on flat surface of the polymeric product and the reading was recorded. The durometer reading was 32 on a scale of 'OOO'.

Example 18

The purpose of this study was to characterize the hemostatic properties of a novel formulation developed by MMI and based on FDA approved materials. The proposed treatment for hemorrhage consists of an application based on two interacting components which, when combined expand within 2 minutes to create a hemostatic bandage that conforms to irregular wound surfaces. This hemostatic product does not require the application of direct pressure. Experiments were carried out on 16 female Yorkshire pigs weighing between 30-50 Kg. The hemostasis formulation was injected into the wound cavity having an femoral artery defect caused by a 6 mm aortic punch, followed by a 6"×8" adhesive patch over the wound with formulation. 500 mL Hextend resuscitation fluid was administered to the pigs at 33 mL/min for 15 min. Lactate Ringer's solution at 100 mL/min, for a maximum delivery of 10 L, was administered to maintain MAP (Mean Arterial Pressure) at 60 mm or higher; MAP and heart rate readings were taken for ten minutes before defect creation, and thereafter, for up to 180 min at specified intervals. Throughout the experiment, the following vitals were measured and recorded as a function of time: (a) MAP, (b) Heart rate, (c) $O_2$ saturation. Both pre-treatment and post-treatment blood losses were measured by suctioning out blood from in and around the wound. Tidal $pCO_2$ was monitored throughout to apply the definition of cessation of life. Experiments on pigs were terminated through euthanasia after 2.5 hours, or when clinical death was determined. At the conclusion of each experiment, the damaged artery was isolated and examined for the nature and patency of the defect. Histopathology tests on the subjects and toxicological studies on the formulation reveal no potential harm. With a 100% survival rate at 2.5 hrs and occurrence of hemostasis in ~12 minutes, MMI's new hemo stasis product is a viable answer to the next generation of advanced wound treatments.

Animal Testing

Materials Modification Inc. conducted animal testing in a porcine model to demonstrate efficacy in achieving hemostasis in severely bleeding wounds. Our formulation was subjected to two protocols:
(a) A moderate (typical) bleed (4-8 mL blood loss per minute per kg of the subject weight), 150-minute survivability protocol; and
(b) A severe bleed (8.01-20 mL blood loss per minute per kg of the subject weight), 90-minute survivability protocol intended to establish the failure limits of the application.

Figure 6:
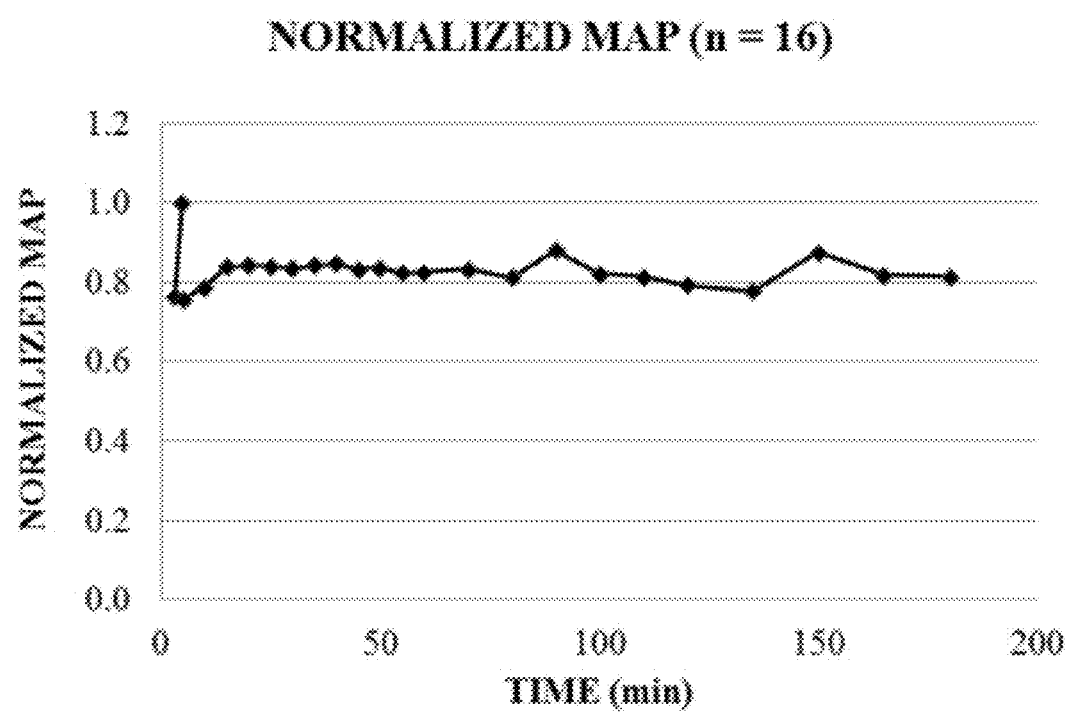
FIG. 6 is a graphical illustration of normalized mean arterial pressure versus time in porcine tests (number of pigs=16) carried out using components A and B.
Figure 7:
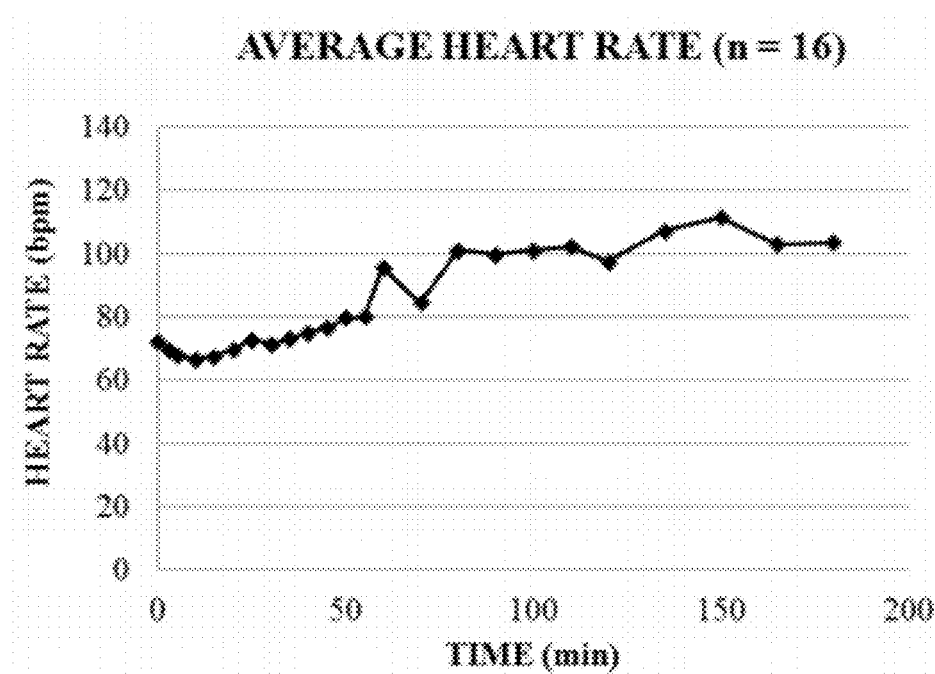
FIG. 7 is a graphical illustration of average heart rate versus time in porcine tests (number of pigs=16) carried out using components A and B.
Figure 8:
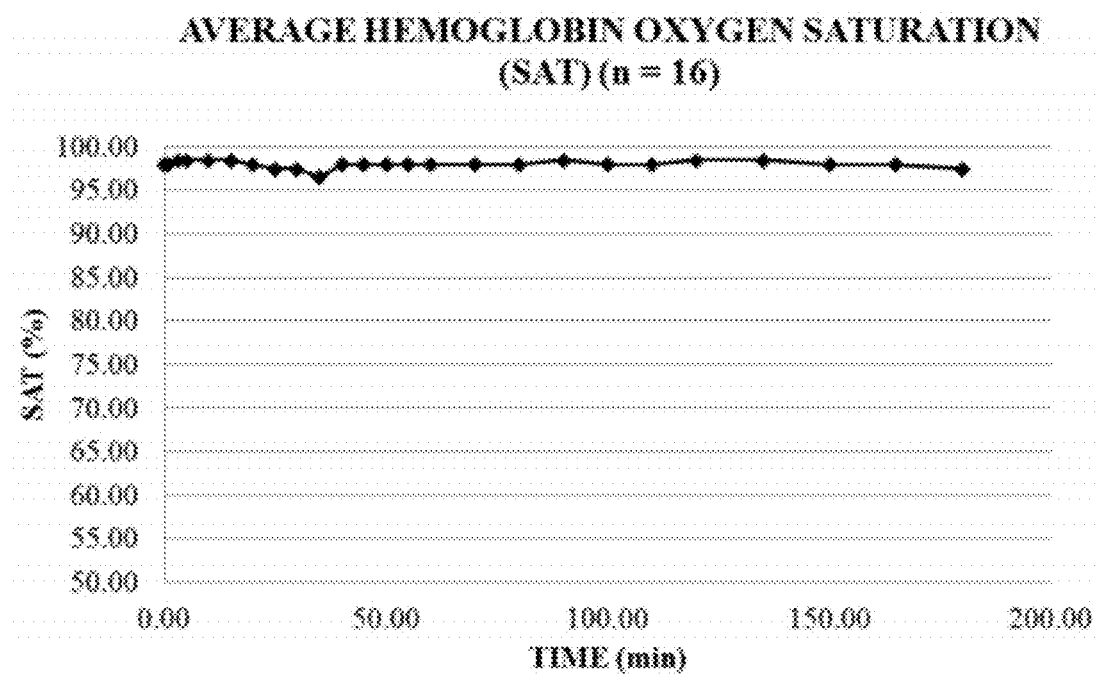
FIG. 8 is a graphical illustration of average hemoglobin oxygen saturation (SAT) versus time in porcine tests (number of pigs=16) carried out using components A and B.

The results for both the tests (N=23) are summarized in Table 48 and FIGS. 6 to 8 below.

TABLE 48

| Number of Pigs Tested | Average Pig Weight (kg) | Survival Time (2.5 hours) | Survival Time (2.0 hours) | Survival Time (1.5 hours) | Success (%) | Average Time to Hemostasis (minute) |
|---|---|---|---|---|---|---|
| 16 (Moderate Bleed) | 36.7 ± 4.5 | 15 | 15 | 15 | 93.75 | 9.2 ± 3.2 |
| 7 (Severe Bleed) | 36.7 ± 4.5 | 0 | 1 | 5 | 85.71 | 14.5 ± 3.5 |

The results showed an overall success rate of 95.65% for tests carried on pigs. Note that "Success" is defined as having the subject animal survive for at least 90 minutes after the application of the hemostatic bandage formulation during moderate and severe bleed experiments. The surviving animals in the moderate and severe bleed groups demonstrated a 6× (or, 600%) and 4× (or, 400%) improvements, respectively, in survival time, compared to the animals receiving no treatment within their same moderate and high bleed grouping. The overall results show that 22 of the total 23 animal subjects (nearly 96%) achieved a "Golden Hour" survival time, considered a crucial (60-minute) period within which exsanguinations from severe wounds, particularly battlefield injuries, must be brought under control, to present the best chances for long-term recovery.

Example 19

Biocompatibility

The cured product is a biocompatible hemostatic wound dressing and as such, it falls under "Surface Devices, Breached or Compromised Surfaces, Category A (Limited contact). The product is a limited contact device because it is intended for emergency use only and is intended to be removed once the patient has received medical attention. As recommended by ISO 10993-1 and FDA Blue Book Memorandum G95-1, the following biocompatibility tests have been conducted on the polymeric foam product: Cytotoxicity, Sensitization and Irritation/Intracutaneous Reactivity. Because the product is intended for use as hemostatic wound dressing, hemolysis testing was also conducted. The material has been shown to pass all tests. A summary of biocompatibility test results are provided below.

The testing was performed by NAMSA (North American Science Associates, Inc. Northwood, Ohio). To prepare the test sample, the closure cap was removed from the dual syringe and the static mixing tip was attached. The contents were dispensed by applying pressure on the dual plunger component. The test article was dispensed and allowed to react for 3 minutes and then allowed to set for a minimum of 54 minutes. The test article was then extracted according to the standard procedures used for each test. The material was shown to pass all tests. A summary of each biocompatibility test follows.

Cytotoxicity Study Using the ISO Elution Method

IX Minimal Essential Media Extract: This in vitro study was conducted to evaluate the product for potential cytotoxic effects following the guidelines of ISO 10993-5: Biological Evaluation of Medical Devices, Part 5: Tests for In Vitro Cytotoxicity. A single preparation of the test article was extracted in single strength Minimum Essential Medium, (IX MEM) at 37° C. for 24 hours. The negative control, reagent control, and positive control were similarly prepared. Triplicate monolayers of L-929 mouse fibroblast cells were dosed with each extract and incubated at 37° C. in the presence of 5% $CO_2$ for 48 hours. Following incubation, the mono layers were examined microscopically for abnormal cell morphology and cellular degeneration. The test article extract showed no evidence of causing cell lysis or toxicity. The test article extract met the requirements of the test since the grade was less than a grade 2 (mild reactivity).

ISO Maximization Sensitization Study 0.9% Sodium Chloride Solution Extract, ISO Maximization Sensitization Study—Sesame Oil, NF Extract: The test article was evaluated for the potential to cause delayed dermal contact sensitization in a guinea pig maximization test. This study was conducted based on the requirements of ISO 10993-10, Biological Evaluation of Medical Devices—Part 10: Tests for Irritation and Skin Sensitization. The test article was extracted in 0.9% sodium chloride USP and sesame oil, NF. Each test article extract was intradermally injected and occlusively patched to ten test guinea pigs (per test article extract). The extraction vehicle (vehicle control) was similarly injected and occlusively patched to five control guinea pigs (per vehicle control). Following a recovery period, the test and control animals received a challenge patch of the appropriate test article extract and the vehicle control. All sites were scored for dermal reactions at 24 and 48 hours after patch removal. The test article extracts showed no evidence of causing delayed dermal contact sensitization in the guinea pig. The test article extracts were not considered a sensitizer in the guinea pig maximization test.

ISO Intracutaneous Study 0.9% Sodium Chloride Solution Extract, ISO Intracutaneous Study—Sesame Oil, NF Extract: The potential for the test article to cause irritation following intracutaneous injection in rabbits was evaluated based on ISO 10993-10: Biological Evaluation of Medical Devices—Part 10: Tests for Irritation and Skin Sensitization. The test article was extracted in 0.9% sodium chloride USP solution (SC) and sesame oil, NF (SO). A 0.2 mL dose of the appropriate test article extract was injected intracutaneously into five separate sites on the right side of the back of each of three animals. Similarly, the extract vehicle alone (control) was injected on the left side of the back of each animal. The injection sites were observed immediately after injection. Observations for erythema and edema were conducted at 24, 48, and 72 hours after injection. The test article met the requirements of the test since the difference between each test extract overall mean score and corresponding control overall mean score was 0.0 and 0.5 for the SC and SO test extracts, respectively.

ISO Acute Systemic Toxicity Study 0.9% Sodium Chloride Solution Extract, ISO Acute System Toxicity Study, Sesame Oil, NS Extract: The test article was evaluated for acute systemic toxicity in mice (*Mus musculus*/Strain: Hla®: (ICR) CVF®) based on ISO 10993-11, Biological Evaluation of Medical Devices—Part 11: Tests for Systemic Toxicity. The test article was extracted in 0.9% sodium chloride USP solution and sesame oil, NF. A single dose of the appropriate test article extract was injected into a group of five animals. Similarly, a separate group of five animals was dosed with each corresponding extraction vehicle alone (control). The animals were observed for signs of systemic toxicity immediately after injection and at 4, 24, 48 and 72 hours after injection. Body weights were recorded prior to dosing and on days 1, 2 and 3. There was no mortality or evidence of systemic toxicity from the extracts. The test article extracts met the requirements of the study.

ASTM Hemolysis

CMF-PBS Extract: The test article was evaluated for the potential to cause hemolysis according to procedures based on ASTM F756, Standard Practice for Assessment of Hemolytic Properties of Materials and ISO 10993-4, Biological Evaluation of Medical Devices—Part 4: Selection of Tests for Interactions with Blood. Anticoagulated whole rabbit blood was pooled, diluted, and added to tubes with the test article in calcium and magnesium-free phosphate buffered saline (CMF-PBS) or in tubes with a CMF-PBS test article extract. Negative and positive controls and blanks were prepared in the same manner. Following incubation for at least 3 hours at 37° C., the tubes were centrifuged, and the supernatant collected. The supernatant was mixed with Drabkin's reagent and the resulting solution was analyzed using a spectrophotometer at a wavelength of 540 nm. The hemolytic index for the test article in direct contact with blood and the test article extract was 0.0%. The test article in direct contact with blood and the test article extract were nonhemolytic.

Example 20

Expansion Time and Reactivity Temperature: Time to expansion, and temperature generated throughout the expansion and curing cycle, are important indicators of the product's effectiveness. Expansion time and reactivity temperature are benchmarks against which long-term lifecycle performance can be measured. The exothermic nature of the expansion and curing of the hemostatic product generates heat in the sample mass that can be transferred to the wound surfaces. The product's tightly controlled reaction time and level, creates a warming action within the wound. Specifically, the curing and expansion of the product hemostatic matrix were balanced to maintain a maximum temperature below 123° Fahrenheit, eliminating the danger of burning in wounds, while supporting a slight warming of the wound site to improve hemostatic conditions. A maximum temperature of between 98 degrees Fahrenheit and 120 degrees Fahrenheit is ideal. It is important to note that temperatures recorded during bench testing can be up to 20° Fahrenheit warmer than those measured empirically during porcine trials.

Example 21

Basic Physical Characteristics of Viscosity versus Functionality: Viscosity has a direct influence on dispensing time, relative volumetric proportioning, and the quality of mixing through the static mix exit nozzle. Ideally, components "A" and "B" need to be dispensed in a 50:50 proportion (+/−5% to 8%). Achieving adequate wound filling, and mixing velocity through the exit nozzle, requires that at least 25 mL to 35 mL each, of Components "A" and "B", be driven into the wound cavity within 25 seconds to 30 seconds (+/−5.0 Seconds). Maintaining consistent product viscosity has a direct bearing on consistent functionality. Each manufacturing lot of the components "A" and "B" is subjected to viscometer testing using a BROOKFIELD Viscometer model #DV-II+ Pro. Typical measuring conditions and test readings are shown in Table 49.

TABLE 49

| FORMU-LATION | Key Test Conditions | 5 RPM | 10 RPM | 20 RPM |
|---|---|---|---|---|
| Component A | Torque | 85% | 30.4% | 49.1% |
| | Temperature | 24.9° C. | 25.1° C. | 25.2° C. |
| | Viscosity (cP) | 1,766-1,905 | 1,776-1786 | 1,766-1,791 |
| Component B | Torque | 11.4% | 11.8% | 16.2% |
| | Temperature | 25.8° C. | 25.9° C. | 24.9° C. |
| | Viscosity (cP) | 2,242-2,262 | 1,151-1,181 | 610-600.3 |

Example 22

Sterilization

Sterilization of all components is achieved by gamma irradiation. Sterilization validation has met the requirements of ANSI/AAMI/ISO 11137, "Sterilization of Healthcare Products—Requirements for Validation and Routine Control—Radiation Sterilization."
  (a) SAL=$10^{-6}$
  (b) Radiation dose=25-50 kGy Shelf Life: Components A and B are designed for an 18-month shelf life, with a manufacture's recommended storage temperature range of 0° C. to 26° C. Despite the care taken to transport and safeguard medical supplies by the military, there are occasions, while supplying combat operations in forward deployments, where the recommended storage temperature ranges may be exceeded. In-field carry conditions, during active maneuvers, require stability and functionality between −10° C. to 40° C. for minimum two-week period. For this reason, the components stability and functional reactivity testing were conducted in laboratory between −28° C. and 60° C.

Stability/Effectiveness Testing Protocol—Approximately 12-Month Duration:
Conditions—Four swing cycle conditions were monitored and repeated 8 times:
Swing Cycle-1) Cold Cycling between −28° C. and 20° C.
Swing Cycle-2) Heat Cycling between +20° C. and 60° C.
Swing Cycle-3) Full Range Cycling between −28° C. and 60° C.
Constant Cycle-4) Control held at a constant 20° C.:
Each temperature swing cycle was standardized to a 96-hour period composed of:
Swing Period-1) 24 hour RAMP to HIGH swing cycle temperature
Swing Period-2) 24 hour HOLD at HIGH swing cycle temperature
Swing Period-3) 24 hour DOWN SLIDE to LOW swing cycle temperature
Swing Period-4) 24 hour HOLD at LOW swing cycle temperature
Repeat Swing Cycling—8 times Repeatation of Swing Periods 1-4 (30 days) performed
Sample Preparation
  (4) sets of (24) samples each, of dual-chamber cartridges, in finished packages, containing the delivery device, and the hydrocolloid Wound Barrier Shield were evaluated. The sets of (24) samples each, were deployed as: Set-1) Cold Cycle set; Set-2) Heat Cycle set; Set-3) Full Range Cycle set; Set-4) Constant temperature "Control" set.
Methodology
  The 96-hour temperature swing cycles, and the constant "Control" temperature cycle, ran continuously and simultaneously. At the end of (8) 96-hour cycles, (2) samples from each of the temperature swing cycle groups, and (2) samples from the constant temperature "Control" group were randomly pulled for reaction testing. The sample pairs from the temperature Swing Cycles (1-3), are tested against the Constant Cycle "Control" for comparative analysis.
Comparative Measures
  There are four primary reactivity characteristics that established time series data for comparison:
  1) Reaction time to reach full expansion and curing
  2) Temperature profile during expansion and curing
  3) Estimated expansion volume
  4) Final durometer
  5) Observations were made for any indications of material separation, or settling
  Subsequent 8 of the 96-hour sampling sessions were compared to previous reactivity test sessions to identify degradation trends among the primary reactivity characteristics.

Example 23

Histological Evaluations of the Polymeric Product

The animal studies permitted histological evaluation of the wound. A pathology report was prepared by Histo-Scientific Research Laboratories (HSRL). Histopathological analysis of tissue samples from two pigs was performed.

Methods

According to the study design, all animals were sacrificed on Day 1. The following organs were harvested for histopathology: A) Femoral artery; B) Muscle; C) Nerve. Collected tissues from both animals were sent to HSRL in Mount Jackson, Va., where they were processed, embedded in paraffin, sectioned and stained with hematoxylin and eosin (H&E). The resulting slides were evaluated at HSRL in Frederick, Md. Microscopic findings, when present, were graded subjectively on a scale of 0 to 4 according to the intensity and extent of change, where 0=finding not present; where 1 is minimal; 2 is mild; 3 is moderate and 4 is marked. Tabulated microscopic data is presented in Table 50.

Histopathology Results:

Macroscopic Observations

There were no macroscopic observations reported by the Testing Facility.

Microscopic Observations

Procedure-related findings were present in skeletal muscle. Minimal multifocal degeneration of the myofibers occurred in the skeletal muscle from both tested animals (Animals 4558 and 4561). In addition, minimal interstitial hemorrhage and mixed inflammatory infiltrates were present in the skeletal muscle from one animal (Animal 4558). The sciatic nerve and femoral artery were unremarkable.

The objective of this study was to evaluate the effectiveness of the hemostatic bandage product to control severe bleeding and promote animal survival for at least 1 to 2.5 hours using a controlled wounding model established by US Army injury research protocols. Under the conditions of this study, there were no microscopic findings related to the administration of hemostatic formulation. The microscopic findings present in the skeletal muscle were considered to be related to the procedure.

TABLE 50

| | BWEF Animal Number | |
| --- | --- | --- |
| | 4558 | 4561 |
| ORGAN/Finding | n/a | n/a |
| ARTERY | N | N |
| NERVE | N | N |
| MUSCLE | | |
| Interstitial hemorrhage, multifocal | 1 | 0 |
| Myofiber degeneration, multifocal | 1 | 1 |
| Mixed inflammatory cell infiltrate, multifocal | 1 | 0 |

N = Normal;
0 = Finding not present;
1 = Minimal;
n/a = not applicable

While this invention has been described as having preferred sequences, ranges, steps, order of steps, materials, structures, shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A two-fluid component injection device for in situ formation of a soft solid artificial blockage to control moderate to severe bleeding, the two-fluid component injection device comprising two isolated chambers, wherein the two isolated chambers comprise a first isolated chamber and a second isolated chamber, the two-fluid component injection device comprising:
   a) the first isolated chamber comprising a first fluid component, the first fluid component comprising:
      i) about 75-90% by weight or volume of at least one siloxane polymer;
      ii) about 0.5-25% by weight or volume of at least one siloxane polymer curing agent;
      iii) about 12-18% by weight or volume of a metal mixture selected from the group consisting of 1) calcium oxide and iron oxides, and, 2) calcium hydroxide and iron oxides; and,
      iv) about 0-25% of a surfactant;
   b) the second isolated chamber comprising a second fluid component, the second fluid component comprising:
      i) about 75-85% by weight or volume of at least one siloxane polymer;
      ii) about 1-20% by weight or volume of hydrogen peroxide;
      iii) about 0-25% of a surfactant;
   wherein the device comprises a mixing tip for mixing the first fluid component and the second fluid component in the two-fluid component injection device to form an active hemostatic dressing, the active hemostatic dressing being injectable into a wound to form the soft solid artificial blockage within the wound,
   wherein the first fluid component and the second fluid component are kept separately within the two isolated chambers of the two-fluid component injection device until mixed within the mixing tip for application into the wound,
   wherein the iron oxides in the mixture function as negative co-catalysts in the decomposition of hydrogen peroxide,
   wherein the siloxane polymer curing agent in the first fluid component is selected from the group consisting of platinum, tin, palladium, rhodium, and respective compounds, salts, complexes thereof, and a combination thereof,
   wherein the soft solid artificial blockage conforms to irregular wound surfaces, and the hydrogen peroxide in the soft solid artificial blockage is less than 5% by weight or volume.

2. The two-fluid component injection device of claim 1, wherein the siloxane polymer curing agent in said first fluid component is present at about 0.5-3% by weight or volume.

3. The two-fluid component injection device of claim 1, wherein the hydrogen peroxide in said second fluid component comprises about 5-18% by weight or volume.

4. The two-fluid component injection device of claim 1, wherein said second fluid component further comprises about 0-10% by weight or volume of a particle filler.

5. The two-fluid component injection device of claim 4, wherein the particle filler in said second fluid component comprises at least one member selected from the group consisting of silicon oxide, fumed silica, titanium dioxide, diatomaceous earth, calcium silicate, aluminum silicate, zeolite, mesoporous material, clay, polyhedral oligomeric silsesquioxane, a chemical and functional derivative of polyhedral oligomeric silsesquioxane, and a combination thereof.

6. A two-fluid component injection device for in situ formation of a soft solid artificial blockage to control moderate to severe bleeding, the two-fluid component injection device comprising two isolated chambers, wherein the two isolated chambers comprise a first isolated chamber and a second isolated chamber, the two-fluid component injection device comprising:
- a) the first isolated chamber comprising a first fluid component, the first fluid component comprising:
  - i) about 84% by weight or volume of at least one siloxane polymer;
  - ii) about 0.5-2% by weight or volume of at least one surfactant;
  - iii) about 0.5-3% by weight or volume of at least one siloxane polymer curing agent; and
  - iv) about 12-18% by weight or volume of a metal mixture selected from the group consisting of 1) calcium oxide and iron oxides, and, 2) calcium hydroxide and iron oxides;
- b) the second isolated chamber comprising a second fluid component, the second fluid component comprising:
  - i) about 82% by weight or volume of at least one siloxane polymer;
  - ii) about 0.5-2% by weight or volume of at least one surfactant;
  - iii) about 17.5% by weight or volume of hydrogen peroxide; and
  - iv) about 0.2% by weight or volume of at least one particle filler.

7. A soft solid hemostatic blockage composition formed in situ by using a two-fluid component injection device to control moderate to severe bleeding, the two-fluid component injection device comprising two isolated chambers, wherein the two isolated chambers comprise a first isolated chamber and a second isolated chamber, the two-fluid component injection device comprising:
- a) the first isolated chamber comprising a first fluid component, the first fluid component comprising:
  - i) about 75-90% by weight or volume of at least one siloxane polymer;
  - ii) about 0-25% by weight or volume of at least one surfactant;
  - iii) about 0.5-25% by weight or volume of at least one siloxane polymer curing agent; and
  - iv) about 12-18% by weight or volume of a metal mixture selected from the group consisting of 1) calcium oxide and iron oxides, and, 2) calcium hydroxide and iron oxides;
- b) the second isolated chamber comprising a second fluid component, the second fluid component comprising:
  - i) about 75-85% by weight or volume of at least one siloxane polymer;
  - ii) about 0-25% by weight or volume of at least one surfactant;
  - iii) about 1-20% by weight or volume of hydrogen peroxide; and
  - iv) about 0-10% by weight or volume of at least one particle filler, wherein the soft solid hemostatic blockage composition conforms to irregular wound surfaces.

8. A soft solid hemostatic blockage composition formed in situ by using a two-fluid component injection device to control moderate to severe bleeding, the two-component injection device comprising two isolated chambers, wherein the two isolated chambers comprise a first isolated chamber and a second isolated chamber, the two-fluid component injection device comprising:
- a) the first isolated chamber comprising a first fluid component, the first fluid component comprising:
  - i) about 84% by weight or volume of at least one siloxane polymer;
  - ii) about 0.5-2% by weight or volume of at least one surfactant;
  - iii) about 0.5-3% by weight or volume of at least one siloxane polymer curing agent; and
  - iv) about 12-18% by weight or volume of a metal mixture selected from the group consisting of 1) calcium oxide and iron oxides, and, 2) calcium hydroxide and iron oxides;
- b) the second isolated chamber comprising a second fluid component, the second fluid component comprising:
  - i) about 82% by weight or volume of at least one siloxane polymer;
  - ii) about 0.5-2% by weight or volume of at least one surfactant;
  - iii) about 17.5% by weight or volume of hydrogen peroxide; and
  - iv) about 0.2% by weight or volume of at least one particle filler, wherein the soft solid hemostatic blockage composition conforms to irregular wound surfaces.

9. A method for in situ formation of a soft solid artificial blockage in a wound or body cavity to control moderate to severe bleeding, comprising injecting from a two-fluid component injection device into the wound or body cavity, a composition that forms a soft solid artificial blockage within the wound, the two-fluid component injection device comprising two isolated chambers, wherein the two isolated chambers comprise a first isolated chamber and a second isolated chamber, the two-fluid component injection device comprising:
- a) the first isolated chamber comprising a first fluid component, the first fluid component comprising:
  - i) about 75-90% by weight or volume of at least one siloxane polymer;
  - ii) about 0.5-25% by weight or volume of at least one siloxane polymer curing agent;
  - iii) about 12-18% by weight or volume of a metal mixture selected from the group consisting of 1) calcium oxide and iron oxides, 2) calcium hydroxide and iron oxides; and,
  - iv) about 0-25% of a surfactant;
- b) the second isolated chamber comprising a second fluid component, the second fluid component comprising:
  - i) about 75-85% by weight or volume of at least one siloxane polymer;
  - ii) about 1-20% by weight or volume of hydrogen peroxide;
  - iii) about 0-25% by weight or volume of a surfactant;

wherein the injecting comprises mixing the first and second fluid components within a mixing tip in the two-fluid component injection device to form an active hemostatic dressing, the active hemostatic dressing being injectable into the wound to form the soft solid artificial blockage within the wound, wherein the first fluid component and the second fluid component are kept separately within the two isolated chambers of the two-fluid injection device until mixed within the mixing tip for application into the wound, wherein the iron oxides in the mixture function as negative co-catalysts in the decomposition of hydrogen peroxide, wherein the siloxane polymer curing agent in the first fluid component is selected from the group consisting of platinum, tin, palladium, rhodium, and respective compounds, salts, complexes thereof, and a combination thereof, wherein the soft solid artificial blockage conforms to irregular wound surfaces, and the hydrogen peroxide in the soft solid artificial blockage is less than 5% by weight or volume; and allowing the composition to penetrate the wound or body cavity and expand therein to form a soft solid artificial blockage within the wound, and wherein the hydrogen peroxide in the soft solid artificial blockage is less than 5% by weight or volume.

10. The method of claim 9, wherein mixing within the mixing tip comprises mechanical or micro-kinetic mixing, or a combination thereof.

11. The method of claim 9, wherein the soft solid artificial blockage is substantially set in about 0 to 60 minutes.

12. The method of claim 9, wherein the soft solid artificial blockage is substantially cross-linked and cured in less than 300 seconds.

13. The method of claim 9, wherein the soft solid artificial blockage has an expansion volume of about 150-800%.

14. The two-fluid component injection device of claim 1, wherein mixing the first component and the second component results in at least 2 times expansion in situ.

15. The two-fluid component injection device of claim 1, wherein the hydrogen peroxide is completely reacted after mixing of the first component and the second component.

16. The two-fluid component injection device of claim 1, wherein the second component comprises about 8.5% by weight or volume of hydrogen peroxide.

17. The two-fluid component injection device of claim 1, wherein the artificial blockage comprises about 5% hydrogen peroxide.

18. The two-fluid component injection device of claim 1, wherein mixing the first component and the second component results in temperature below 123° F.

19. The two-fluid component injection device of claim 1, wherein the first fluid component comprises about 0.5-2% by weight or volume of at least one surfactant.

20. The two-fluid component injection device of claim 1, wherein the second fluid component comprises about 0.5-2% by weight or volume of at least one surfactant.

21. The two-fluid component injection device of claim 1, wherein the surfactant of the first fluid component comprises at least one member selected from the group consisting of polyether, polyol-polyether mixture, fluoro surfactant, fluoro surfactant and polyether polymer, nonylphenoxypoly(ethylene oxy)ethanol, polyoxyethylene sorbitan monolaurate, polyoxythylene sorbitan monostearate, polyoxyethylene sorbitan monooleate, and a combination thereof.

22. The two-fluid component injection device of claim 1, wherein the surfactant of the second fluid component comprises at least one member selected from the group consisting of polyether, polyol-polyether mixture, fluoro surfactant, fluoro surfactant and polyether polymer, polyoxyethylene sorbitan monolaurate, polyoxythylene sorbitan monostearate, polyoxyethylene sorbitan monooleate, and a combination thereof.

23. The two-fluid component injection device of claim 1, wherein the siloxane polymer of the first fluid component is selected from the group consisting of poly(dimethylsiloxane) vinyl terminated, polydimethylsiloxane (PDMS), divinyltetramethyldisiloxane, and, di methylsiloxane, and, wherein the siloxane polymer of the second fluid component is selected from the group consisting of poly (dimethylsiloxane) vinyl terminated, polydimethylsiloxane (PDMS), divinyltetramethyldisiloxane, methylhydrosiloxane, dimethylsiloxane, and, methylhydrosiloxane-dimethylsiloxane copolymer.

24. The two-fluid component injection device of claim 6, wherein the siloxane polymer of the first fluid component is selected from the group consisting of poly(dimethylsiloxane) vinyl terminated, polydimethylsiloxane (PDMS), divinyltetramethyldisiloxane, and, dimethylsiloxane, and, wherein the siloxane polymer of the second fluid component is selected from the group consisting of poly (dimethylsiloxane) vinyl terminated, polydimethylsiloxane (PDMS), divinyltetramethyldisiloxane, methylhydrosiloxane, dimethylsiloxane, and, methylhydrosiloxane-dimethylsiloxane copolymer.

25. The two-fluid component injection device of claim 7, wherein the siloxane polymer of the first fluid component is selected from the group consisting of poly(dimethylsiloxane) vinyl terminated, polydimethylsiloxane (PDMS), divinyltetramethyldisiloxane, and, dimethylsiloxane, and, wherein the siloxane polymer of the second fluid component is selected from the group consisting of poly (dimethylsiloxane) vinyl terminated, polydimethylsiloxane (PDMS), divinyltetramethyldisiloxane, methylhydrosiloxane, dimethylsiloxane, and, methylhydrosiloxane-dimethylsiloxane copolymer.

26. The two-fluid component injection device of claim 8, wherein the siloxane polymer of the first fluid component is selected from the group consisting of poly(dimethylsiloxane) vinyl terminated, polydimethylsiloxane (PDMS), divinyltetramethyldisiloxane, and, dimethylsiloxane, and, wherein the siloxane polymer of the second fluid component is selected from the group consisting of poly (dimethylsiloxane) vinyl terminated, polydimethylsiloxane (PDMS), divinyltetramethyldisiloxane, methylhydrosiloxane, dimethylsiloxane, and, methylhydrosiloxane-dimethylsiloxane copolymer.

27. The method of claim 9, wherein the siloxane polymer of the first fluid component is selected from the group consisting of poly(dimethylsiloxane) vinyl terminated, polydimethylsiloxane (PDMS), divinyltetramethyldisiloxane, and, dimethylsiloxane, and, wherein the siloxane polymer of the second fluid component is selected from the group consisting of poly (dimethylsiloxane) vinyl terminated, polydimethylsiloxane (PDMS), divinyltetramethyldisiloxane, methylhydrosiloxane, dimethylsiloxane, and, methylhydrosiloxane-dimethylsiloxane copolymer.

28. The two-fluid component injection device of claim 1, wherein the soft solid artificial blockage has a durometer reading of hardness on a scale of "OOO".

29. The two-fluid component injection device of claim 28, wherein the durometer reading is 32 on a scale of "OOO".

* * * * *